United States Patent
Zhou et al.

(10) Patent No.: US 12,113,498 B2
(45) Date of Patent: Oct. 8, 2024

(54) SIGNAL PROCESSING CIRCUITS AND DEVICES

(71) Applicant: SHENZHEN SHOKZ CO., LTD., Guangdong (CN)

(72) Inventors: Xin Zhou, Shenzhen (CN); Lei Su, Shenzhen (CN); Yuxiang Zhang, Shenzhen (CN); Meiqi Li, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 52 days.

(21) Appl. No.: 18/181,575

(22) Filed: Mar. 10, 2023

(65) Prior Publication Data

US 2023/0216486 A1    Jul. 6, 2023

Related U.S. Application Data

(63) Continuation of application No. PCT/CN2021/102851, filed on Jun. 28, 2021.

(30) Foreign Application Priority Data

Dec. 31, 2020 (WO) ................ PCT/CN2020/142529

(51) Int. Cl.
*A61B 5/305* (2021.01)
*A61B 5/00* (2006.01)
*H03H 11/04* (2006.01)

(52) U.S. Cl.
CPC ........... *H03H 11/04* (2013.01); *A61B 5/7225* (2013.01); *A61B 5/725* (2013.01); *A61B 5/305* (2021.01); *H03H 2011/0488* (2013.01)

(58) Field of Classification Search
CPC .. A61B 5/24; A61B 5/30; A61B 5/305; A61B 5/72; A61B 5/7225; A61B 5/725; H03H 11/04; H03H 11/0488
See application file for complete search history.

(56) References Cited

U.S. PATENT DOCUMENTS

| | | | |
|---|---|---|---|
| 5,318,039 A | 6/1994 | Kadefors et al. | |
| 2005/0215916 A1* | 9/2005 | Fadem | A61B 5/31 600/509 |

(Continued)

FOREIGN PATENT DOCUMENTS

| | | |
|---|---|---|
| CN | 2938573 Y | 8/2007 |
| CN | 101119115 A | 2/2008 |

(Continued)

OTHER PUBLICATIONS

International Search Report in PCT/CN2021/102851 mailed on Sep. 23, 2021, 7 pages.

(Continued)

*Primary Examiner* — William Hernandez
(74) *Attorney, Agent, or Firm* — METIS IP LLC

(57) ABSTRACT

The embodiments of the present disclosure are for a signal processing circuit. The signal processing circuit includes an analog circuit. The analog circuit is used for processing an initial signal it receives. The initial signal includes a target signal and a noise signal. The analog circuit includes a first processing circuit and a second processing circuit. The first processing circuit is used to increase a ratio of the target signal to the noise signal, and output a first processed signal. The second processing circuit is used to amplify the first processed signal. A gain multiple of the second processing circuit to the first processed signal varies with a frequency of the first processed signal. The first processing circuit includes a common mode signal suppression circuit used to (Continued)

suppress a common mode signal in the initial signal, a low-pass filter circuit, and a high-pass filter circuit.

20 Claims, 21 Drawing Sheets

(56) References Cited

U.S. PATENT DOCUMENTS

| | | | |
|---|---|---|---|
| 2007/0073184 A1* | 3/2007 | Lu | A61B 5/7239 |
| | | | 600/544 |
| 2010/0145217 A1 | 6/2010 | Otto et al. | |
| 2013/0150697 A1 | 6/2013 | Imai et al. | |
| 2014/0114205 A1 | 4/2014 | Braun et al. | |
| 2015/0257645 A1 | 9/2015 | Bae et al. | |
| 2016/0051186 A1 | 2/2016 | Kaib et al. | |
| 2016/0120428 A1 | 5/2016 | Yoshida et al. | |
| 2017/0111123 A1 | 4/2017 | Ouzounov | |
| 2018/0310887 A1 | 11/2018 | Deng | |
| 2019/0150777 A1 | 5/2019 | Guo et al. | |
| 2020/0028532 A1 | 1/2020 | Sen et al. | |

FOREIGN PATENT DOCUMENTS

| | | |
|---|---|---|
| CN | 104142583 A | 11/2014 |
| CN | 105125211 A | 12/2015 |
| CN | 106301659 A | 1/2017 |
| CN | 106419880 A | 2/2017 |
| CN | 106872849 A | 6/2017 |
| CN | 107510454 A | 12/2017 |
| CN | 111317456 A | 6/2020 |
| EP | 3536228 A1 | 9/2019 |
| EP | 3545823 A1 | 10/2019 |
| JP | 2005287820 A | 10/2005 |
| JP | 3132458 U | 6/2007 |
| KR | 20010001629 A | 1/2001 |
| WO | 2020236147 A1 | 11/2020 |

OTHER PUBLICATIONS

Written Opinion in PCT/CN2021/102851 mailed on Sep. 23, 2021, 6 pages.
International Search Report in PCT/CN2020/142529 mailed on Oct. 12, 2021, 8 pages.
Written Opinion in PCT/CN2020/142529 mailed on Oct. 12, 2021, 6 pages.
Notice of Reasons for Rejection in Japanese Application No. 2023-524766 mailed on Apr. 22, 2024, 21 pages.
The Extended European Search Report in European Application No. 21912961.6 mailed on Feb. 26, 2024, 9 pages.

* cited by examiner

400C

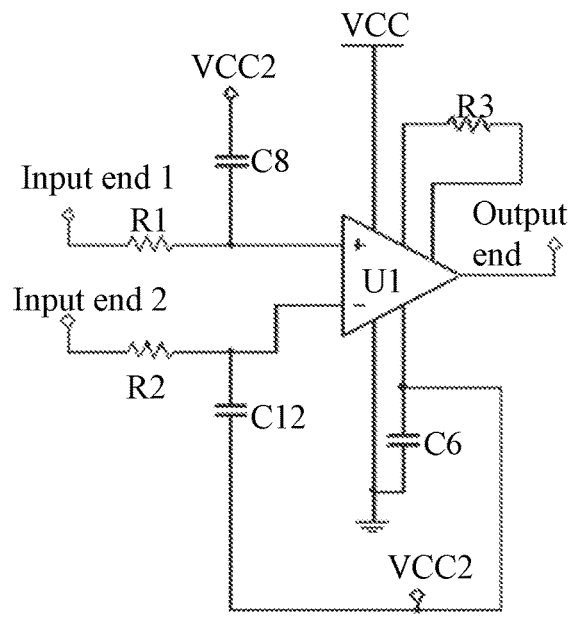
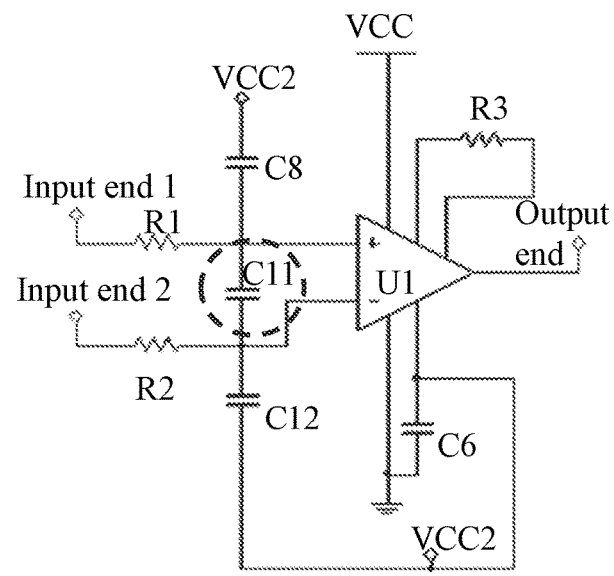
FIG. 5A  FIG. 5B
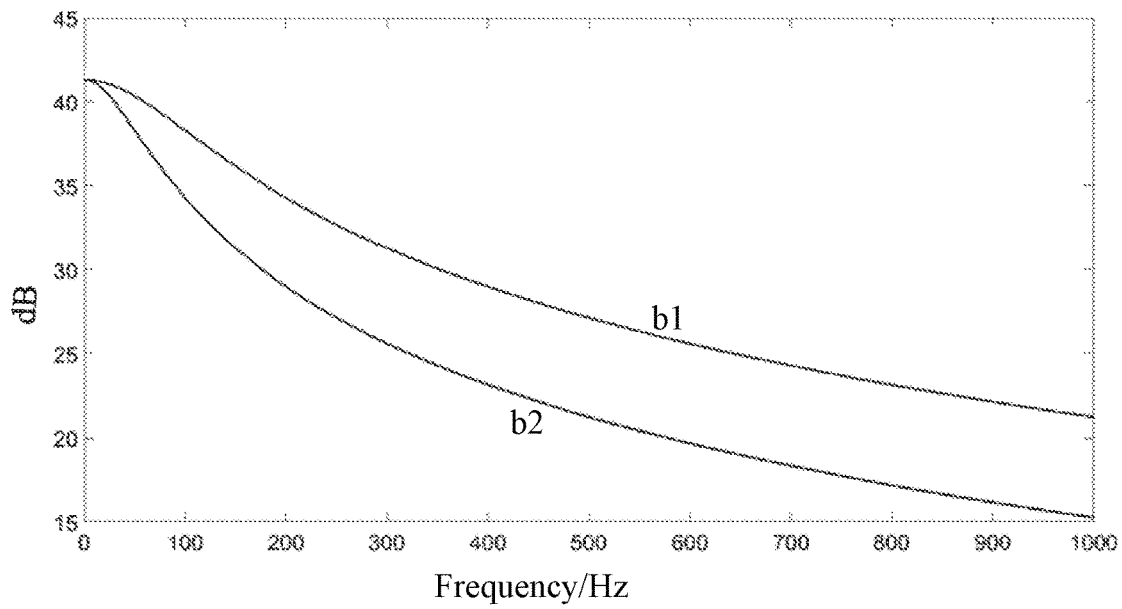
FIG. 5C

600

900A

900B

SIGNAL PROCESSING CIRCUITS AND DEVICES

CROSS-REFERENCE TO RELATED APPLICATIONS

This application is a continuation of International Patent Application No. PCT/CN2021/102851 filed on Jun. 28, 2021, which claims priority to International Patent Application No. PCT/CN2020/142529 filed on Dec. 31, 2020, the entire contents of each of which are hereby incorporated by reference.

TECHNICAL FIELD

The present application generally relates to the field of circuit design, and in particular, to a circuit and a device for processing physiological signals.

BACKGROUND

As people pay more and more attention scientifically to sports and physiological health, the demand for physiological signal monitoring devices also increases. Some physiological signals (for example, a myoelectric signal of a user when the user is exercising) are weak in output strength. In the presence of noise, it may be difficult for a general signal processing circuit to retain an effective physiological signal after removing the noise. Therefore, it is desirable to provide a signal processing circuit suitable for a physiological signal monitoring device which can process a specific physiological signal in a targeted manner.

SUMMARY

The embodiments of the present disclosure provide a signal processing circuit. The signal processing circuit may comprise of an analog circuit. The analog circuit may be configured to process an initial signal received by the analog circuit. The initial signal may comprise of a target signal and a noise signal. The analog circuit may include a first processing circuit and a second processing circuit connected to the first processing circuit. The first processing circuit may be configured to increase a ratio of the target signal to the noise signal and output a first processed signal. The second processing circuit may be configured to amplify the first processed signal, and the gain multiple of the second processing circuit to the first processed signal varies with a frequency of the first processed signal. The first processing circuit may include a common mode signal suppression circuit, a low-pass filter circuit, and a high-pass filter circuit. The common mode signal suppression circuit may be configured to suppress a common mode signal in the initial signal.

In some embodiments, the common mode signal suppression circuit may comprise of a differential amplifier.

In some embodiments, the low-pass filter circuit may include a bridge circuit structure formed at an input end of the differential amplifier.

In some embodiments, an input impedance of the differential amplifier may be greater than 10 MΩ.

In some embodiments, an upper cut-off frequency point of the low-pass filter circuit may be within a frequency range of 100 Hz-1000 Hz.

In some embodiments, a lower cut-off frequency point of the high-pass filter circuit may be within a frequency range of 5 Hz-200 Hz.

In some embodiments, the first processing circuit may comprise a notch circuit for suppressing a power frequency signal.

In some embodiments, the notch circuit may comprise a cascaded notch circuit, and the cascaded notch circuit may be also used to suppress one or more harmonics in the power frequency signal.

In some embodiments, the notch circuit may comprise a dual-T active notch circuit.

In some embodiments, the first processing circuit may further comprise a voltage-controlled low-pass filter circuit, the voltage-controlled low-pass filter circuit may be configured to provide a gain near a target frequency of the voltage-controlled low-pass filter circuit and may be combined with the low-pass filter circuit to compensate an attenuation of the low-pass filter circuit.

In some embodiments, the increasing the ratio of the target signal to the noise signal by the first processing circuit may comprise: performing amplification processing of a first amplification factor on the target signal; and performing attenuation processing on the noise signal.

In some embodiments, the second processing circuit may comprise of an amplifier circuit, a feedback circuit, and a follower. The amplifier circuit may be configured to amplify the first processed signal by a second amplification factor, the second amplification factor being greater than the first amplification factor. The follower may be configured to isolate an influence of an output end of the signal processing circuit.

In some embodiments, the second processing circuit may have a greater gain response to the first processed signal in a first frequency range than that of a frequency range outside the first frequency range.

In some embodiments, the first frequency range may include 20 Hz-140 Hz.

In some embodiments, the initial signal may comprise a myoelectric signal.

In some embodiments, the signal processing circuit may further comprise of a control circuit, a switch circuit, and at least two signal acquisition circuits. The at least two signal acquisition circuits may be configured to acquire at least two initial signals. The switch circuit may be configured to control a conduction between the at least two signal acquisition circuits and the analog circuit, so that initial signals acquired by a part of the at least two signal acquisition circuits are transmitted to the analog circuit at the same time. The control circuit may be configured to receive the target signal processed by the analog circuit, and sample the processed target signal.

In some embodiments, the switch circuit may include a plurality of input channels, and each signal acquisition circuit in the at least two signal acquisition circuits may be independently connected to one input channel, and the switch circuit selects only one input channel to be conducted at the same time based on a control signal of the control circuit.

In some embodiments of the present disclosure provides a signal processing device. The signal processing device may include a signal processing circuit. The signal processing circuitry may comprise an analog circuit. The analog circuit may be configured to process an initial signal received by the analog circuit. The initial signal may comprise a target signal and a noise signal. The analog circuit may include a first processing circuit and a second processing circuit connected to the first processing circuit. The first processing circuit may be configured to increase a ratio of the target signal to the noise signal and output a first processed signal. The second processing circuit may be configured to amplify the first processed signal, and the gain multiple of the second processing circuit to the first processed signal varies with a frequency of the first processed signal. The first processing circuit may include a common mode signal suppression circuit, a low-pass filter circuit, and a high-pass filter circuit. The common mode signal suppression circuit may be configured to suppress a common mode signal in the initial signal.

Additional features will be set forth in part in the description which follows and will become apparent to those skilled in the art upon examination of the following contents and accompanying drawings, or may be learned by production or operation of the examples. The features of the present disclosure may be realized and obtained by practicing or using various aspects of the methods, means and combinations set forth in the following detailed examples.

BRIEF DESCRIPTION OF THE DRAWINGS

The present disclosure will be further described in the form of exemplary embodiments, which will be described in detail by the accompanying drawings. These embodiments are not restrictive. In these embodiments, the same number represents the same structure, wherein:

FIG. 5A-5B are schematic structural diagrams of low-pass filter circuits according to some embodiments of the present disclosure;

FIG. 5C is a frequency response curve diagram of the low-pass filter circuits in FIG. 5A and FIG. 5B;

DETAILED DESCRIPTION

Figure 1:
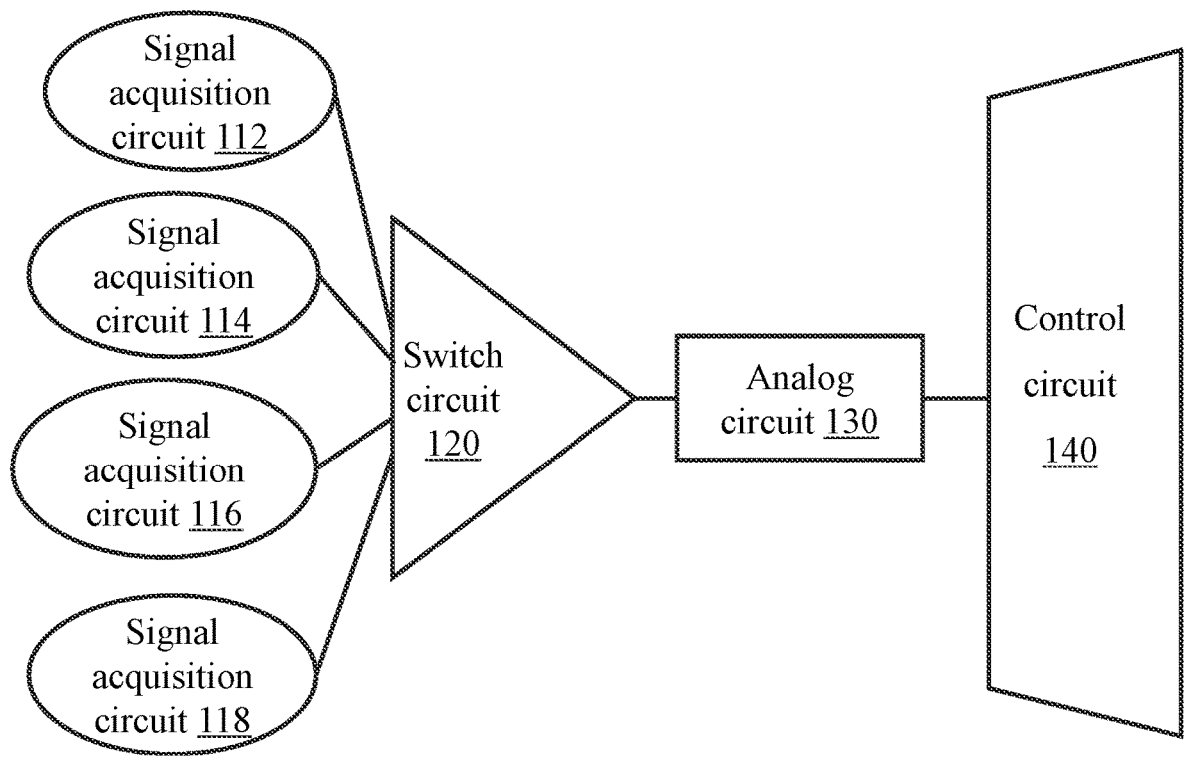
FIG. 1 is a schematic diagram of an exemplary circuit of a signal acquisition device according to some embodiments of the present disclosure.

In order to more clearly explain the technical scheme of the embodiments of the present disclosure, the following will briefly introduce the drawings that need to be used in the description of the embodiments. Obviously, the drawings in the following description are only some examples or embodiments of the present disclosure. For those skilled in the art, the present disclosure can also be applied to other similar scenarios based on these drawings without creative work. The same label of each electronic device in the figure can represent different electronic devices, which are only used to distinguish each device in the same embodiment. For example, the same reference R1 may represent resistors of different resistances.

As indicated in the present disclosure and claims, the terms "a," "an," "an" and/or "the" do not refer to the singular and may include the plural unless the context clearly indicates an exception. Generally speaking, the terms "comprise" and "include" only suggest the inclusion of clearly identified steps and elements, and these steps and elements do not constitute an exclusive list. Methods or devices may also contain other steps or elements.

It should be understood that the terms "data block," "system," "engine," "unit," "component," "module" and/or "block" used herein are used to distinguish different components, elements, parts or assemblies at different levels. However, if other words can achieve the same purpose, they can be replaced by other expressions.

Various terms are used to describe the spatial and functional relationships between elements (for example, between layers), including "connection," "interface," and "coupling". Unless explicitly described as "direct," when describing a relationship between first and second elements in the present disclosure, the relationship includes a direct relationship between the first and second elements without other intermediate elements, and the indirect relationship between the first and second elements with one or more intermediate elements (spatially or functionally). In contrast, when an element is said to be "directly" connected, bonded, interfaced, or coupled to another element, there is no intermediate element. In addition, spatial and functional relationships between elements can be realized in various ways. For example, a mechanical connection between two components may include a welded connection, a key connection, a pin connection, an interference fit connection, or any combination thereof. Other words used to describe the relationship between elements should be interpreted in a similar way (for example, "between," "between . . . ," "adjacent" and "directly adjacent").

The signal processing circuits and methods described in the embodiments of the present disclosure may be applied to a signal monitoring device that needs to collect one or more signal sources, especially a physiological signal monitoring device, such as an intelligent wearable device. In some embodiments, the intelligent wearable device (for example, a suit, a wrist guard, a shoulder belt, etc.) may be set at various parts of the human body (for example, a calf, a thigh, the waist, the back, a chest, a shoulder, the neck, etc.) to collect physiological signals of various parts of a user's body when the user is in different states. Subsequently, the intelligent wearable device may further process the acquired signals. In some embodiments, the physiological signal may be a signal that can be detected to reflect a state of the body, for example, the physiological signal may include a respiratory signal, an ECG signal, an EMG signal, a blood pressure signal, a temperature signal, and any other signal. In some embodiments, a frequency range of the physiological signal may include 0.05 Hz to 2 kHz, wherein a frequency range of the ECG signal may include 0.05 Hz to 100 Hz, and a frequency range of the EMG signal may include 5 Hz to 2 kHz.

In some embodiments, in order to effectively retain a target signal (for example, an EMG signal) in an acquired signal during processing, the acquired signal may be denoised in advance before the noise signal reaches saturation to prevent the subsequent noise from being amplified to the saturation state and resulting in the loss of the target signal. In addition, by processing the acquired signal with noise reduction before amplification, more processing margin can be left for the target signal.

The embodiments of the present disclosure provide a signal processing circuit. The signal processing circuit may include an analog circuit. The analog circuit may be used to process an initial signal the analog circuit receives. The initial signal may include a target signal and a noise signal. The analog circuit may include a first processing circuit and a second processing circuit connected with the first processing circuit. The first processing circuit may be configured to improve a signal-to-noise ratio of the initial signal to output a first processed signal. The second processing circuit may be configured to amplify the first processed signal, and a gain multiple of the second processing circuit to the first processed signal may vary with the frequency of the first processed signal. The first processing circuit may include a common mode signal suppression circuit, a low-pass filter circuit, and/or a high-pass filter circuit. The common mode signal suppression circuit may be configured to suppress a common mode signal in the input signal.

In some embodiments, if an abnormal situation occurs in a physiological signal acquisition process, a noise signal in the acquired signal may annihilate an effective physiological signal during signal processing (for example, amplification processing). If the acquired signal is, for example, amplified before the noise signal is eliminated, the circuit may be saturated and the physiological signal may not be effectively extracted. For example, a power frequency signal (noise) may be introduced in the process of acquiring the EMG signal. Since the strength of the power frequency signal is far greater than the strength of the EMG signal (the former may reach a ten-volt level, while the latter may only have a millivolt level), if an acquisition electrode is abnormal (for example, the electrode falls off, the electrode is lifted, etc.) during the acquisition of the EMG signal, the EMG signal in the final acquired signal may be annihilated by the power frequency signal. Therefore, according to some embodiments of the present disclosure, the physiological signal is denoised by the first processing circuit first, and then the physiological signal after noise reduction is amplified by the second processing circuit, which may prevent abnormal situations in the physiological signal acquisition process from causing circuit saturation in the processing process, so as to obtain accurate and high-quality physiological signals.

FIG. 1 is a schematic diagram of an exemplary circuit of a signal acquisition device according to some embodiments of the present disclosure. The circuit 100 of the signal acquisition device may realize the acquisition and processing of multiple physiological signals. Compared with a multi-channel scheme, the circuit 100 adopts a time-sharing multiplexing scheme, which may save space and economic costs, save hardware resources such as ADC, and prevent crosstalk under the condition of ensuring the acquisition and processing of multiple signal sources. Specifically, as described in FIG. 1, the circuit 100 may include at least two signal acquisition circuits (for example, signal acquisition circuits 112, 114, 116, and 118), a switch circuit 120, an analog circuit 130, and a control circuit 140.

The switch circuit 120 may be set between the multiple signal acquisition circuits and the analog circuit 130, which may be configured to control a conduction state between each signal acquisition circuit and the analog circuit 130. For example, at a certain time point, the switch circuit 120 may conduct a signal acquisition circuit and the analog circuit 130. Within a certain time range, the switch circuit 120 may conduct each signal acquisition circuit and the analog circuit 130 in a periodic manner. When the switch circuit 120 conducts a certain signal acquisition circuit and the analog circuit 130, a signal (for example, the EMG signal) acquired by the signal acquisition circuit may be transmitted to the analog circuit 130 for processing (for example, noise reduction, amplification, etc.), and the processed signal may be transmitted to the control circuit 140 for signal analysis. It can be understood that by setting the switch circuit 120 between the multiple signal acquisition circuits and the analog circuit 130, the same analog circuit may process the signals acquired by different signal acquisition circuits at different time points, which may effectively reduce the complexity and cost of using multiple analog circuits, and also reduce a number of signal transmission channels between subsequent analog circuits and control circuits. It should be noted that the switch circuit 120 and analog circuit 130 shown in FIG. 1 are merely for the purpose of illustration. In actual use, more than one switch circuit or analog circuit may be configured between the multiple signal acquisition circuits and the control circuit 140, and these switch circuits or analog circuits may still achieve a process similar to the above description.

In some embodiments, the at least two signal acquisition circuits may be configured to acquire at least two target signals. The target signal may be a physiological signal (e.g., one or more of a respiratory signal, an ECG signal, an EMG signal, a blood pressure signal, a temperature signal, etc.) that can reflect the user's physical state. Merely by way of example, different signal acquisition circuits may respectively include one or more electrodes in contact with the user's body, through which the EMG signals on the user's body surface may be acquired. Different signal acquisition circuits may be arranged at different positions of the user's body to collect the same or different physiological signals of the user. For example, the signal acquisition circuits arranged at different sides of the users thigh may be configured to collect the EMG signals at the thigh. As another example, the signal acquisition circuit arranged at the user's forearm may be configured to collect the EMG signal at the forearm, while the signal acquisition circuit arranged at the user's heart may be configured to collect the user's ECG signal. It should be noted that under certain scenarios, the circuit 100 or similar circuits may be configured to acquire and process the same or different physiological signals mentioned above, which is not limited in the present disclosure. In some embodiments, the at least two signal acquisition circuits may include only two signal acquisition circuits, or three signal acquisition circuits, four signal acquisition circuits, or more signal acquisition circuits. In some embodiments, the frequency range of the physiological signal may include 0.05 Hz to 2 kHz, wherein the frequency range of the ECG signal may include 0.05 Hz to 100 Hz, and the range of the EMG signal may include 5 Hz to 2 kHz.

The control circuit 140 may sample a signal processed by the analog circuit 130. In some embodiments, a sampling frequency of the control circuit 140 may be related to the number of signal acquisition circuits, a control strategy of the switch circuit 120, and a target frequency. For example, the sampling frequency of the control circuit 140 for each signal may be not less than 2 times the target frequency of the control circuit 140. As an example, for an EMG signal, if the corresponding target frequency is within 1000 Hz, the control circuit 140 may sample the EMG signal with a sampling frequency of 2000 Hz. For the circuit 100, if there are four signal acquisition circuits for acquiring the EMG signals, the control circuit 140 may need to provide a total sampling frequency of 8000 Hz, so as to ensure that the sampling rate of each EMG signal can reach 2000 Hz. As another example, as mentioned elsewhere in the present disclosure, the control circuit 140 may control the switching of the switch circuit 120 by adopting a complete reconstruction strategy and a strength characterization strategy. In the complete reconstruction strategy, the sampling frequency may be related to the number of signal acquisition circuits, a rising edge time or a falling edge time of a single channel, etc., wherein the rising edge time and the falling edge time of a single channel may be related to an output voltage amplitude (which may be related to an amplification factor and an input voltage amplitude) of the analog circuit 130 and a voltage swing rate of circuit components.

In some embodiments, the switch circuit 120 may be configured to control the conduction between the at least two signal acquisition circuits and the analog circuit 130, so that only part of the target signals acquired by the signal acquisition circuits in the at least two signal acquisition circuits may be transmitted to the analog circuit 130 at the same time. An input end of the switch circuit 120 may be connected with the at least two signal acquisition circuits, and an output end of the switch circuit 120 may be connected with the analog circuit 130. In some embodiments, the switch circuit 120 may include multiple input channels, and each signal acquisition circuit in the at least two signal acquisition circuits may be connected to an input channel separately. At the same time, the switch circuit 120 may select an input channel to be conducted based on a control signal of the control circuit 140.

In some embodiments, the switch circuit 120 may adopt a switch chip with multi-channel and dual output, such as a TMUX1209 switch chip. Merely by way of example, the switch circuit 120 may realize time-sharing multiplexing of four channels through three control pins, wherein one pin EN is marked as enabling, and the other two pins A1 and A0 are marked as selecting channels. Four input channels of the switch circuit 120 may be respectively used to connect with the signal acquisition circuits to collect the target signals, and an output port of the switch circuit 120 may be connected to the analog circuit 130. In some embodiments, the gating of the switch chip may be controlled by the values of the control pins (EN, A1, A0). For example, when inputting (1, 0, 0), it may indicate that gating channel A; when inputting (1, 0, 1), it may indicate that gating channel B; when inputting (1, 1, 0), it may indicate that gating channel C; and when inputting (1, 1, 1), it may indicate that gating channel D. Merely by way of example, when the control circuit 140 gates the channel A of the switch circuit 120, the target signal corresponding to the channel A may be connected to the analog circuit 130 and finally sampled by the control circuit 140. When this sampling is successful, the control circuit 140 may give new control instructions, for example, an instruction (1, 0, 1) may be given to gate the channel B, then the target signal of the channel B may be connected to the analog circuit 130 and finally sampled by the control circuit 140, and so on. That is to say, the control circuit 140 may control the switch circuit 120 to switch circularly between the multiple signal acquisition circuits, so as to achieve the function of time-sharing multiplexing. That is, multiple signal sources may be processed in time-sharing through one analog circuit 130, thus saving space costs and reducing hardware requirements.

In different cases, the control circuit 140 may control the switching of the switch circuit 120 based on different strategies. For example, in order to enable subsequent sampled data to completely retain information of each target signal (that is, the control circuit 140 can reconstruct each target signal based on the sampled data), the control circuit 140 may adopt a complete reconstruction strategy to control the switching of the switch circuit 120. Under the complete reconstruction strategy, the control circuit 140 may switch an input channel of the switch circuit 120 according to a total sampling frequency provided by the control circuit 140. For example, a frequency of switching the input channel of the switch circuit 120 may be equal to the sampling frequency provided by the control circuit 140. In this case, every time the switch circuit 120 switches the input channel, that is, every time a signal acquisition circuit is conducted, the control circuit 140 may sample the target signal acquired by the signal acquisition circuit once. Moreover, since the sampling frequency of each target signal by the control circuit 140 is more than twice of the target frequency, the complete reconstruction strategy can ensure that each target signal has at least two sampling points in each cycle. For more details about the complete reconstruction control strategy, please refer to FIG. 2 and the descriptions thereof.

As another example, considering that the control circuit 140 may not be able to obtain effective sampled data during a fast-switching process of the switch channels (because the switching of each switch channel mentioned below may lead to a certain rising edge and falling edge of a signal received by the control circuit 140), the control circuit 140 may use a strength characterization strategy to control the switching of the switch circuit 120. Under the strength characterization strategy, the control circuit 140 may switch the input channels of the switch circuit 120 based on a preset frequency. The preset frequency may be related to a period for the user to implement an action. For example, in order to analyze an EMG signal generated by the muscle when the user performs strength training, the preset frequency may be a certain multiple of a frequency of the user implementing a specific action (for example, horizontal pushing), so that within a period of the user implementing the specific action, the switch circuit 120 may conduct each signal acquisition circuit multiple times, resulting in that the control circuit 140 can sample each target signal multiple times. Under the strength characterization strategy, the control circuit 140 may obtain strength information of each target signal based on sampling results. For more descriptions of the strength characterization strategy, please refer to FIG. 2 and the descriptions thereof.

The analog circuit 130 may be configured to process the received target signal. In some embodiments, since an amplitude of an original target signal directly acquired by the signal acquisition circuit is very small, and there is a lot of noise, the analog circuit 130 may be required to perform processing such as filtering, differential amplification, amplification, negative feedback denoising on the original target signal. In some embodiments, the analog circuit 130 may also be referred to as a signal processing circuit. In some embodiments, the analog circuit 130 may include a differential amplifier for suppressing a common mode signal and amplifying the received target signal. In some embodiments, the analog circuit 130 may include a multistage amplifier circuit for multistage amplification of the received target signal. In the multistage amplifier circuit, different amplifier circuits may have different amplification gains for their input signals. For example, in the multistage amplifier circuit of the analog circuit 130, an amplification gain of an amplifier circuit located at a front stage may be smaller than that of an amplifier circuit located at a rear stage. In some embodiments, the analog circuit 130 may include a filter circuit for filtering the received target signal. Exemplary filtering processes may include high-pass filtering, low-pass filtering, bandpass filtering, or filtering to remove specific frequency components. The filtering process may occur before all the amplification processes or between the multistage amplification processes. In some embodiments, the analog circuit 130 may include a right leg drive circuit, which may be configured to extract the common mode signal in the target signal the right leg drive circuit receives, and feedback the common mode signal back to the signal source after reverse amplification, so as to mainly suppress the power frequency in the signal source. In some embodiments, the analog circuit 130 may include a differential amplifier, a multistage amplifier, a filter circuit, and a right leg drive circuit, or only one or more of them. More descriptions of the signal processing circuit can be found elsewhere in the present disclosure (for example, FIGS. 3A-12C and the descriptions thereof).

As described above, the control circuit 140 may be configured to receive the target signal processed by the analog circuit 130 and sample the processed target signal. In some embodiments, the control circuit 140 may include a plurality of analog-digital conversion channels (i.e., ADC channels). Each ADC channel may be configured to convert the received target signal processed by the analog circuit 130 into a digital signal for reading and processing. In some embodiments, the control circuit 140 may also be connected with a display device to display the read digital signal, so as to intuitively reflect the physiological signal. In some embodiments, based on the sampling, the control circuit 140 may read, store, process, and analyze the target signal. Optionally, the control circuit 140 may also issue a corresponding instruction according to the sampled data.

In some embodiments, the sampling of each processed target signal by the control circuit 140 may occur after a period of time after the control circuit 140 starts to receive the processed target signal of each channel. That is to say, after the switch circuit 120 switches the conducted channel, the control circuit 140 may not sample the new conducted target signal immediately, or even if the control circuit 140 samples the new conducted target signal, the sampling result may not be taken as a component of the target signal immediately. When target signals of multiple signal sources are acquired by the time-sharing multiplexing manner, the switching of the switch channels may cause the signals received by the control circuit 140 to have a certain rising edge and a falling edge. The rising edge may correspond to a time required for an output signal to rise due to the change of an input signal until the output signal reaches a stable state. The falling edge may correspond to a time required for an output signal to fall due to the change of an input signal until the output signal reaches a stable state. The rising edge and falling edge may be jointly affected by a number of factors, including the response stability speed of the switch circuit 120, a voltage swing of a chip in the circuit, the charging and discharging of capacitors and other devices in the circuit, etc. Therefore, in order to ensure that the target signal read by the control circuit 140 is true and effective, the sampling of the target signal may be carried out after the signal is stable, that is, after the switch circuit 120 switches the conducted channel, the control circuit 140 may not sample the signal during the rising edge time. If the sampling starts without waiting for enough time, the value finally read by the control circuit 140 may be an intermediate transition value. It can be understood that if the rising edge time is fixed, even if the waiting time is insufficient, a ratio of the final transition value to the true value may be consistent, which may also be used for subsequent processing and analysis. However, when the rising edge time is related to a voltage change, if the reading is performed before the signal is stable, a ratio of the value read by the control circuit 140 each time to the true value may be not fixed, which cannot be used for subsequent processing. In addition, it can be understood that if a relationship between the transition value and a stable value is considered clearly, or an error between the transition value and the stable value can be accepted, then even if the waiting time is insufficient, the transition value may also be used for subsequent processing and analysis. In conclusion, the strength of the target signal and the gain of the circuit should be considered to obtain a maximum rising edge time as a reference for the waiting time of the control circuit 140. Specifically, a reference time not less than the maximum rising edge time may be set. The sampling of each target signal by the control circuit 140 may occur after the reference time after the control circuit 140 starts to receive the target signal, or the sampling of the target signal by the control circuit 140 may occur after the reference time after each switch circuit switches the conducted channel.

Figure 2:
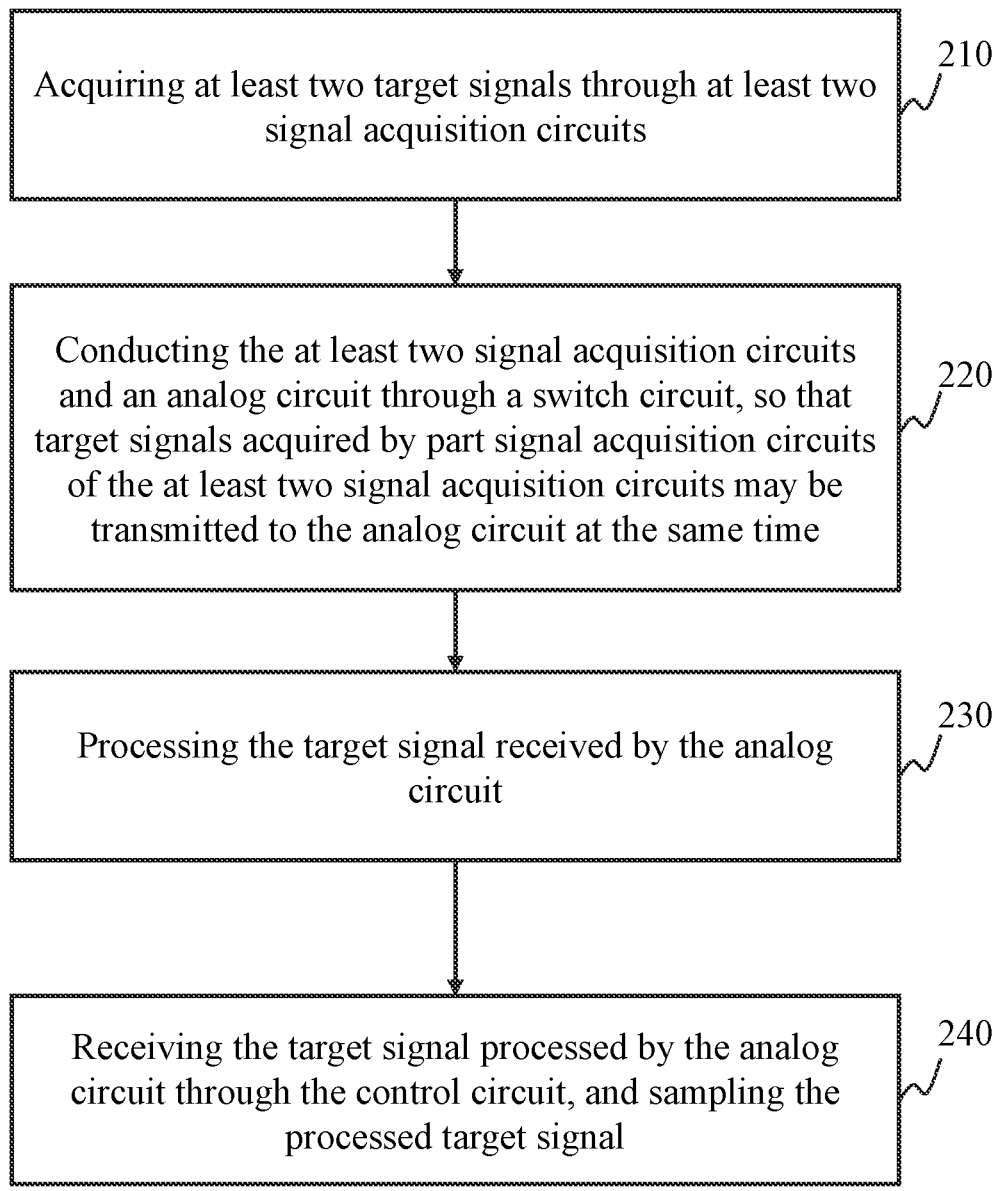
FIG. 2 is a flowchart of an exemplary signal processing method according to some embodiments of the present disclosure.

FIG. 2 is a flowchart of an exemplary signal processing method according to some embodiments of the present disclosure. In some embodiments, the process 200 may be implemented by the circuit 100.

In 210, at least two target signals may be acquired through at least two signal acquisition circuits. In some embodiments, operation 210 may be implemented by the at least two signal acquisition circuits (e.g., signal acquisition circuits 112, 114, 116, and 118) in the circuit 100.

In some embodiments, the at least two signal acquisition circuits may be configured to acquire the at least two target signals. The target signal may be a physiological signal that can reflect the user's physical state, such as one or more of a respiratory signal, an ECG signal, an EMG signal, a blood pressure signal, a temperature signal, etc. Merely by way of example, different signal acquisition circuits may respectively include one or more electrodes in contact with the users body, through which the EMG signals on the user's body surface may be acquired. Different signal acquisition circuits may be arranged at different positions of the user's body to acquire the same or different physiological signals of the user. For example, the signal acquisition circuits arranged at different sides of the user's thigh may be configured to collect the EMG signals at the thigh. As another example, the signal acquisition circuit arranged at the user's forearm may be configured to collect the EMG signal at the forearm, while the preference acquisition circuit arranged at the user's heart may be configured to collect the user's ECG signal. It should be noted that under certain scenarios, the circuit 100 or similar circuits may be configured to collect and process the same or different physiological signals mentioned above, which is not limited in the present disclosure. In some embodiments, the at least two signal acquisition circuits may include only two signal acquisition circuits, or three signal acquisition circuits, four signal acquisition circuits, or more signal acquisition circuits. In some embodiments, a frequency range of the physiological signal may include 0.05 Hz to 2 kHz, wherein the frequency range of the ECG signal may include 0.05 Hz to 100 Hz, and the frequency range of the EMG signal may include 5 Hz to 2 kHz.

In 220, the at least two signal acquisition circuits and an analog circuit may be conducted through a switch circuit, so that target signals acquired by part signal acquisition circuits of the at least two signal acquisition circuits may be transmitted to the analog circuit at the same time. In some embodiments, operation 220 may be implemented by the switch circuit 120 in the circuit 100.

In some embodiments, an input end of the switch circuit may be connected with the at least two signal acquisition circuits, and an output end of the switch circuit may be connected with the analog circuit (for example, the analog circuit 130). In some embodiments, the switch circuit may include a plurality of input channels. Each of the at least two signal acquisition circuits may be connected to an input channel separately. At the same time, the switch circuit may select an input channel to be conducted based on a control signal of the control circuit (for example, the control circuit 140).

In some embodiments, the switch circuit may implement the conduction between each signal acquisition circuit and the analog circuit based on a control instruction of the control circuit. Taking the time-sharing multiplexing of four channels described above as an example, when the control circuit 140 gates the channel A of the switch circuit 120, the target signal corresponding to the channel A may be connected to the analog circuit 130 and finally sampled by the control circuit 140. When this sampling is successful, the control circuit 140 may give a new control instruction, for example, an instruction may be given to gate the channel B, then the target signal of the channel B may be connected to the analog circuit 130, and finally sampled by the control circuit, and so on. That is to say, the control circuit 140 may control the switch circuit 120 to switch circularly between the multiple signal acquisition circuits, so as to achieve the function of time-sharing multiplexing. That is, multiple signal sources may be processed in time-sharing through one analog circuit 130, thus saving space costs and reducing hardware requirements.

In 230, the target signal received by the analog circuit may be processed. In some embodiments, operation 230 may be implemented by the analog circuit 130 in the circuit 100.

In some embodiments, since an amplitude of an original target signal directly acquired by the signal acquisition circuit is very small, and there is a lot of noise, the analog circuit 130 may be required to perform processing such as filtering, differential amplification, amplification, negative feedback denoising on the original target signal. In some embodiments, the analog circuit 130 may include a differential amplifier for suppressing a common mode signal and amplifying the received target signal. In some embodiments, the analog circuit 130 may include a multistage amplifier circuit for amplifying the received target signal. In some embodiments, the analog circuit 130 may include a filter circuit for filtering the received target signal. In some embodiments, the analog circuit 130 may include a right leg drive circuit, which may be configured to extract the common mode signal in the target signal the right leg drive circuit receives, and feedback the common mode signal back to the signal source after reverse amplification, so as to mainly suppress the power frequency in the signal source. In some embodiments, the analog circuit 130 may include a differential amplifier, a multistage amplifier, a filter circuit, and a right leg drive circuit, or only one or more of them.

In some embodiments, considering that there may be baseline drift, the problem of baseline drift may be solved by reducing a gain of the analog circuit to the target signal (i.e., reducing an amplification factor in the analog circuit), and/or selecting a control chip with a high-precision ADC channel, and/or selecting a resistor to adjust a reference potential, and/or the baseline shift may be filtered out by selecting a method of adding a high-pass filter in the analog circuit 130.

In 240, the target signal processed by the analog circuit may be received through the control circuit, and the processed target signal may be sampled. In some embodiments, operation 240 may be implemented by the control circuit 140 in the circuit 100.

In some embodiments, the control circuit 140 may include a plurality of ADC channels, each ADC channel may be configured to convert the received target signal processed by the analog circuit 130 into a digital signal for reading and processing. In some embodiments, the control circuit 140 may also be connected with a display device to display the read digital signals, so as to intuitively reflect the physiological signals. In some embodiments, based on the sampling, the control circuit 140 may read, store, process, and analyze the target signal. Optionally, the control circuit 140 may also issue a corresponding instruction according to the sampled data.

In some embodiments, the sampling of each processed target signal by the control circuit 140 may occur after a period of time after the control circuit 140 starts to receive the processed target signal of each channel. That is to say, after the switch circuit 120 switches the conducted channel, the control circuit 140 may not sample the new conducted target signal immediately, or even if the control circuit 140 samples the new conducted target signal, the sampling result may not be taken as a component of the target signal immediately.

In some embodiments, the sampling frequency of the control circuit 140 may be related to the number of signal acquisition circuits, a type of target signal, and the target frequency of the target signal. For example, the sampling frequency of each signal by the control circuit 140 may be not less than 2 times the target frequency of the target signal. Merely by way of example, for the EMG signal, if the corresponding target frequency is within 1000 Hz, the control circuit may sample the EMG signal with an adopted frequency of 2000 Hz. For the whole signal processing circuit, if there are four acquisition circuits for acquiring EMG signals, the control circuit 140 may need to provide a total sampling frequency of 8000 Hz, so as to ensure that the sampling rate of each EMG signal can reach 2000 Hz.

In different cases, the control circuit 140 may control the switching of the switch circuit 120 based on different strategies.

In some embodiments, in order to enable subsequent sampled data to completely retain information of each target signal (that is, the control circuit 140 can reconstruct each target signal based on the sampled data), the control circuit 140 may adopt a complete reconstruction strategy to control the switching of the switch circuit 120. Under the complete reconstruction strategy, the control circuit 140 may switch an input channel of the switch circuit 120 according to a total sampling frequency provided by the control circuit 140. For example, a frequency of switching the input channel of the switch circuit 120 may be equal to the sampling frequency provided by the control circuit 140. In this case, every time the switch circuit 120 switches the input channel, that is, every time a signal acquisition circuit is conducted, the control circuit 140 may sample the target signal acquired by the signal acquisition circuit once. Moreover, since the sampling frequency of each target signal by the control circuit 140 is more than twice of the target frequency, the complete reconstruction strategy can ensure that each target signal has at least two sampling points in each cycle.

Continuing to take the above four signal acquisition circuits for acquiring EMG signals as an example, assuming that a target frequency of each EMG signal is within 1 kHz, the control circuit may provide a 2 kHz sampling frequency for each EMG signal. For the control circuit, a total sampling frequency of 8 kHz may be provided. The switch circuit may also switch between the four signal acquisition circuits at a frequency of 8 kHz, which may switch once every 125 microseconds, and the control circuit may sample the received EMG signal once every two adjacent switching of the switch circuit.

Furthermore, under the complete reconstruction strategy, the control circuit my completely reproduce the corresponding multiple target signals based on the acquired sampled data. For example, the control circuit may reconstruct each target signal, and further analyze the frequency, phase, intensity (amplitude) and other information in each target signal. Optionally, the control circuit may send the acquired sampled data or the reconstructed target signal to an external processing circuit for analysis in a wired or wireless manner.

In some embodiments, the frequency of the switch circuit 120 switching the input channel may equal to half or other fractional values of the sampling frequency provided by the control circuit 140. In this case, every time the switch circuit 120 switches the input channel, that is, every time a signal acquisition circuit is turned on, the control circuit 140 may sample the target signal acquired by the signal acquisition circuit twice. Continuing to take the above four signal acquisition circuits for acquiring EMG signals as an example, assuming that the target frequency of each EMG signal is within 1 kHz, the control circuit may provide a 2 kHz sampling frequency for each EMG signal. For the control circuit, a total sampling frequency of 8 kHz may be provided. The switch circuit may only need to switch between the four signal acquisition circuits at a frequency of 4 kHz, which may switch once every 250 microseconds. The control circuit may sample the received EMG signals twice between every two adjacent switching of the switch circuit. Compared with the case where the switch circuit only samples once between every two adjacent switchings, for the target signal acquired in this way, since a sampling time point of each channel signal is not uniform enough, there may be some deviation in each channel of target signal reconstructed based on the sampled data.

It should be known that under the above complete reconstruction strategy, a count of channels that can be processed by the control circuit in the time-sharing multiplexing manner may be affected by a rising edge time and a falling edge time of the target signal. Merely by way of example, if the frequency of the target signal is 500 Hz, the control circuit may provide a sampling frequency greater than 1 kHz for a single channel. At this time, a switching speed of the switch circuit may need to reach 4 kHz to realize the four-channel time-sharing multiplexing, and a residence time of the switch circuit in a single channel may be only 250 microseconds, while the switching speed of the switch circuit may need to reach 8 kHz when realizing eight-channel time-sharing multiplexing, and the residence time of the switch circuit in a single channel may be only 125 microseconds. Considering the influence of the rising edge and falling edge, the residence time of the switch circuit in each channel may not be too small. For example, if the rising edge and the falling edge are both 50 microseconds, in this case, a maximum of 16-channel time-sharing multiplexing may be achieved. Therefore, the rising edge time and the falling edge time, the number of channels, and a frequency range of the target signal may be generally considered to select an appropriate number of channels and a corresponding channel switching time.

In other embodiments, considering that the control circuit 140 may not be able to obtain effective sampled data in a fast-switching process of the switch channels (that is, the rising edge and the falling edge of the above signal may cause the switch circuit to stay in a single channel for a long time, and the control circuit may not collect at least two effective data points in a cycle of the target signal), the control circuit 140 may use the strength characterization strategy to control the switching of the switch circuit 120. Under the strength characterization strategy, the control circuit 140 may switch the input channels of the switch circuit 120 based on a preset frequency. The preset frequency may be related to a period for the user to implement an action. For example, in order to analyze an EMG signal generated by the muscle when the user performs strength training, the preset frequency may be a certain multiple of a frequency of the user implementing a specific action (for example, horizontal pushing), so that within a period of the user implementing the specific action, the switch circuit 120 may conduct each signal acquisition circuit multiple times, resulting in that the control circuit 140 can sample each target signal multiple times.

Continuing to take the four signal acquisition circuits for acquiring EMG signals as an example, assuming that the user may execute an action once a second, if the control circuit samples each target signal 10 times under one action, a switching speed of the switch circuit may be 40 times per second. When switching to a signal acquisition circuit each time, the control circuit may wait for the signal to stabilize first, and then may perform continuous sampling until the 25 ms time of the signal is over. In this case, the switching speed of the switch circuit may be independent of the total sampling frequency of the control circuit. The control circuit may use a relatively high total sampling frequency to achieve the effect of acquiring high-frequency signals in the target signal.

Furthermore, under the strength characterization strategy, the control circuit may obtain strength information of the target signal based on the acquired sampled data. For example, under the strength characterization strategy, the control circuit may continuously sample the target signal generated by a single signal acquisition circuit within a period of time. The control circuit may calculate an intensity of the target signal acquired by the signal acquisition circuit during this period based on the continuously sampled data, for example, calculate an average value of the continuously sampled data. Of course, the control circuit may also calculate the strength of the target signal based on all the sampled data corresponding to the signal acquisition circuit. Furthermore, when the control circuit calculates the strength of the target signal corresponding to the same signal acquisition circuit in discontinuous multiple time periods, the control circuit may generate a change relationship between the strength of the target signal and time based on these signal strengths and the corresponding time of these signal strengths, so as to extract specific frequency information of the target signal.

In some embodiments, the strength characterization strategy may collect some frequency information while acquiring strength information. Under this strategy, part of the signal information may be lost due to incomplete acquisition of signals in all time periods, so part of the frequency information may be lost. Merely by way of example, the switch circuit may be controlled at a total frequency of 40 Hz for switching. In the case of four signal acquisition circuits, an acquisition time of each input channel may be 25 ms. At this time, the acquisition of low-frequency signals whose signal frequencies are less than 40 Hz may have some loss. However, if the signals acquired in each segment (i.e., the signal sampled many times after a single channel switching) are processed into a representative value (for example, an average value may be extracted from the signals acquired every 25 ms), and there may be 10 representative values in a single channel within 1 s, signals below 5 Hz may be reconstructed using the processing manner of the complete reconstruction strategy.

In some embodiments, the time-sharing multiplexing capability under the strength characterization strategy may be related to the frequency of the user's action and a monitoring accuracy requirement of the user's action. Due to the single channel acquisition that may last for a long time, the time-sharing multiplexing capability may be less affected by the rising edge and the falling edge. In some embodiments, under this strategy, if the frequency of the target signal is too low, a count of channels for time sharing multiplexing may be limited, so it may also be related to the frequency of the target signal. Since it is necessary to extract the frequency and strength information of the target signal, it may be difficult to collect the low-frequency signal, such as a signal with a frequency below 40 Hz. In this case, the count of channels for time-sharing multiplexing may be reduced, that is, the count of signal acquisition circuits may be reduced.

In some embodiments, the control circuit 140 may adjust a specific switch control strategy according to an actual situation. For example, the control circuit 140 may switch between the complete reconstruction strategy and the strength characterization strategy. The selection or switching between the complete reconstruction strategy and the strength characterization strategy may be judged according to a delay time of the circuit (for example, a rising edge time and a falling edge time) and signal-to-noise ratio requirements of the circuit. For example, when the delay time of the circuit is long, and the target signal frequency, the number of signal acquisition circuits, and an amplification factor of the analog circuit cannot be changed, the control circuit 140 may choose the strength characterization strategy. As another example, when an appropriate filter circuit is added to the analog circuit to improve the signal-to-noise ratio, considering that the filter circuit may cause a longer delay time, the control circuit 140 may choose the strength characterization strategy. On the contrary, when the delay time of the circuit is short or the requirement for the signal-to-noise ratio is not high, the control circuit 140 may choose the complete reconstruction strategy. In some embodiments, the control circuit 140 may adjust the switch control strategy according to environmental factors or user instructions. For example, assuming that different switch control strategies correspond to different power consumption rates, the control circuit 140 may adjust the switch control strategy according to a power status of a power supply (for example, a battery). When the power supply is low, the switch control strategy with a low power consumption rate may be selected. As another example, the control circuit 140 may adjust the switch control strategy according to instructions input by the user to meet different needs of the user.

It should be noted that the above description of the process 200 is only for example and description, and does not limit the scope of the present disclosure. For those skilled in the art, various amendments and changes may be made to the process 200 under the guidance of the present disclosure. However, these amendments and changes are still within the scope of the present disclosure.

Figure 3A:
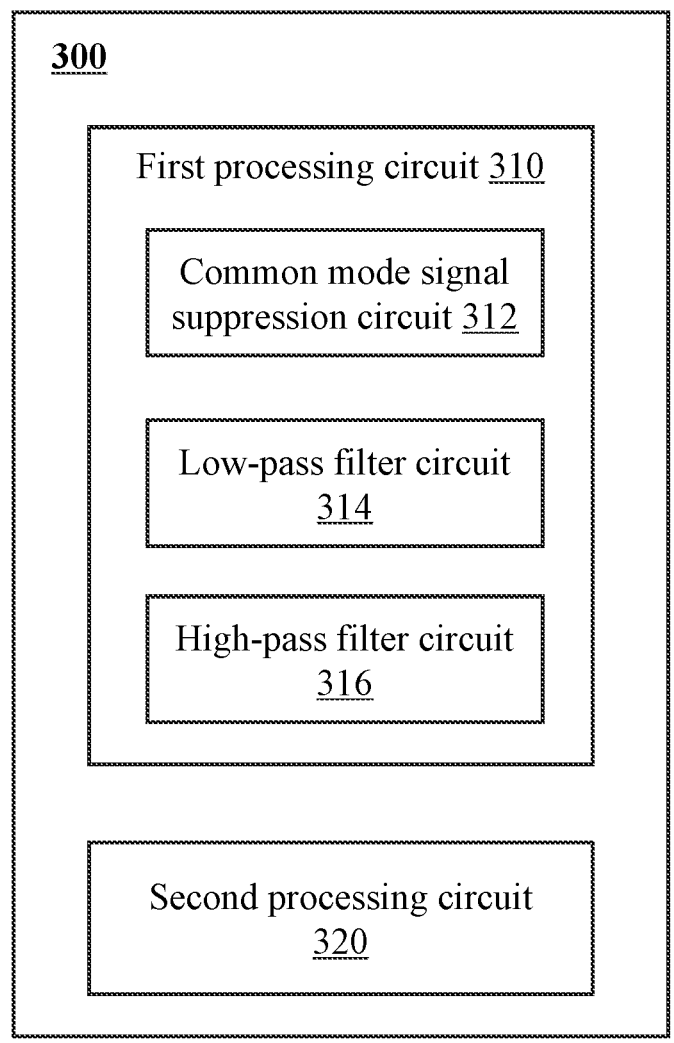
FIG. 3A is a schematic block diagram of an exemplary signal processing circuit according to some embodiments of the present disclosure.

FIG. 3A is a schematic block diagram of an exemplary signal processing circuit according to some embodiments of the present disclosure. As shown in FIG. 3A, the signal processing circuit 300 may include a first processing circuit 310 and a second processing circuit 320 connected to the first processing circuit 310. The signal processing circuit 300 may be configured to process an initial signal the signal processing circuit 300 receives. The initial signal may be a signal acquired by the signal acquisition circuit. In some embodiments, the initial signal may include a target signal and a noise signal. In some embodiments, the first processing circuit 310 and the second processing circuit 320 may be collectively referred to as an analog circuit (e. g., the analog circuit 130).

The first processing circuit 310 may be configured to increase a signal-to-noise ratio (SNR) of the initial signal and output a first processed signal. For example, the first processing circuit 310 may perform a first amplification process on the target signal in the initial signal and an attenuation process on the noise signal in the initial signal. As another example, the first processing circuit 310 may amplify the target signal and noise signal at the same time. An amplification factor for the target signal may be greater than an amplification factor for the noise signal, thereby increasing the signal-to-noise ratio of the signal. The target signal in the initial signal may be a physiological signal that can reflect the user's physical state, such as one or more of a respiratory signal, an ECG signal, an EMG signal, a blood pressure signal, a temperature signal, etc. For the convenience of description, the present disclosure may take the EMG signal as an example of the physiological signal. It should be understood that the data described below for characteristics of the EMG signal does not limit the scope of the present disclosure. For example, when the target signal is an ECG signal, the corresponding strength (amplitude) range and/or frequency range of the target signal may correspond to a data value of the ECG signal. Specifically, the amplitude range of the ECG signal may be 10 μV-4 mV, and the frequency range of the ECG signal may be 0.05 Hz-100 Hz. For those skilled in the art, various corrections and changes may be made to the signal processing circuit 300 under the guidance of the present disclosure to adapt to the processing of the ECG signal.

In some embodiments, the amplitude and/or frequency of EMG signals of different muscles (e.g., pectoralis major, biceps brachii, etc.) or different individuals (e.g., adults, children, etc.) may be different. For example, the amplitudes of the biceps brachii and trapezius may easily reach a millivolt level, while the amplitudes of the latissimus dorsi and abdominal muscles may generally reach a hundred microvolt level. As another example, frequency distributions of EMG signals obtained from explosive force generation and continuous force generation may be different. As further another example, the amplitude and frequency of an EMG signal may also be affected by a degree of muscle fatigue. The amplitude of the EMG signal obtained after muscle fatigue may become larger, and the frequency distribution may be redshifted. In some embodiments, the amplitude of the EMG signal may be in a range of 5 μV-100 mV. In some embodiments, the frequency of the EMG signal may be in a range of 10 Hz-1000 Hz. In some embodiments, the frequency of the EMG signal may be in a range of 10 Hz to 700 Hz. In some embodiments, the frequency of the EMG signal may be in a range of 10 Hz-500 Hz. In some embodiments, the frequency of the EMG signal may be in a range of 20 Hz-500 Hz. In some embodiments, the frequency of the EMG signal may be in a range of 20 Hz-140 Hz. In some embodiments, in order to accurately analyze muscle movement, the obtained EMG signal needs to have characteristics of a high signal-to-noise ratio, good stability, etc. However, due to the complexity of noise signals in the EMG signals and EMG signals of different individuals and muscles are different, it is difficult to obtain complete EMG signals (for example, 10 Hz-1000 Hz EMG signals). Due to the main frequency components (for example, 80%, 90%, etc., of the total frequency components) of different EMG signals are relatively concentrated in the frequency domain (for example, they are mainly distributed in the range of 20 Hz-140 Hz), and analysis results of the EMG signals of the main frequency components may also reflect an accurate muscle movement situation, thus, when processing the acquired EMG signals, only the EMG signals in the main frequency components (also known as a target frequency band) may be extracted to obtain high-quality EMG signals. For the convenience of description, the present disclosure may take 20 Hz-140 Hz as an example of the target frequency band, which does not limit the scope of the present disclosure. It should be noted that when the target frequency band changes, one or more parameters of the signal processing circuit in the present disclosure may also be changed accordingly, thereby making the signal processing circuit applicable to the changed target frequency band.

In some embodiments, the noise signal may include one or more of motion artifacts (MAs), a power frequency signal, a power frequency harmonic signal (i.e., a harmonic signal of the power frequency signal), an aliasing noise, a white noise, etc. For example, if the initial signal is a signal acquired by a signal acquisition circuit (for example, the signal acquisition circuit 112), in addition to acquiring the EMG signal, the signal acquisition circuit (for example, an electrode) may also collect the power frequency signal, the power frequency harmonic signal, the MA, etc. It should be noted that among many noise signals, the intensity of the power frequency signal and/or the power frequency harmonic signal may be much higher than other noise signals, which may bring trouble to the analysis of the target signal. In some cases, the power frequency signal and/or power frequency harmonic signal may saturate the output of the signal processing circuit, which may result in the loss of the target signal if the power frequency signal and/or power frequency harmonic signal are not processed. In some embodiments of the present disclosure, the initial signal may be first processed by the first processing circuit 310 to attenuate the noise signal (such as the MA, the power frequency signal, and the power frequency harmonic signal) and first amplify the target signal in the initial signal, and then the second processing circuit 320 may perform the second amplification processing on the noise attenuated signal, so as to suppress the interference of the noise signal on the target signal. In some embodiments, the signal processing circuit 300 may be connected with a digital circuit to convert the signal processed by the second processing circuit 320 into a digital signal for reading and processing. It should be noted that the further amplification of the processed signal through the second processing circuit 320 may have the following benefits: (1) when the digital circuit has noise, the second processing circuit 320 may improve the overall signal-to-noise ratio; (2) by setting the second processing circuit 320, an ADC accuracy requirement for the digital circuit may be reduced.

The power frequency signal may be generated from a power supply system. In some embodiments, a frequency of the power frequency signal may be 50 Hz, 60 Hz, etc. In the present disclosure, the frequency of the power frequency noise may take 50 Hz as an example for description. In some embodiments, the power supply system may also generate the power frequency harmonic signal. The strength of the power frequency harmonic signal may be weaker than the strength of the power frequency signal. The power frequency harmonic signal may include a power frequency odd harmonic signal and a power frequency even harmonic signal. In other words, the frequency of the power frequency harmonic signal may include 100 Hz, 150 Hz, 200 Hz, 250 Hz, 300 Hz, 350 Hz, 400 Hz, etc. In some embodiments, when the three-phase windings of a power generation system are asymmetric and/or a magnetization curve of an iron core of the power supply system is in a nonlinear saturation state, the presence of non-sinusoidal periodic signals may generate the power frequency harmonic signal. In this case, the odd harmonics may play a dominant role in the power frequency harmonic signal. In other words, the frequency of the power frequency harmonic signal may mainly include 150 Hz, 250 Hz, 350 Hz, 450 Hz, etc.

Since the frequency of the power frequency signal is 50 Hz, which is within the target frequency band (for example, 20 Hz-140 Hz) of the EMG signal, and the strength of the power frequency signal may reach a volt level, the existence of the power frequency signal may have a serious impact on the EMG signal (the signal strength may reach a millivolt level). In addition, since the power frequency signal is extremely strong and the EMG signal is very weak, even if the power frequency harmonic signal is weaker than the power frequency signal, the power frequency harmonic signal may still have a huge impact on the EMG signal. Therefore, in order to suppress the influence of the power frequency signal and the power frequency harmonic signal on the EMG signal, it is necessary to process the power frequency signal and the power frequency harmonic signal. It should be noted that the power frequency signal (frequency is 50 Hz) in the EMG signal (for example, its target frequency band is 20 Hz-140 Hz) cannot be filtered by relying on a high-pass filter alone, because to filter out the frequency component of 50 Hz, the high-pass filter may sacrifice many EMG signals (for example, the EMG signals with frequency in the range of 20-40 Hz). In addition, since the frequency of the power frequency signal is within the range of the target frequency band, in order to better retain the signal of the target frequency band, a high-pass filter with a very narrow transition band may be required, but a high-pass filter with a very narrow transition band may need to be multi-cascaded, which may cost a lot of resources.

In some embodiments of the present disclosure, a common mode signal suppression circuit 312 in the first processing circuit 310 may be used to process the power frequency signal. The common mode signal suppression circuit 312 may be configured to suppress a common mode signal in the initial signal. In the present disclosure, the common mode signal may refer to signals with the same phase and the same amplitude in different signals. Since the power frequency signal comes from the power supply system and the human body can be regarded as a good conductor, the phase and amplitude of the power frequency signal in different signals may be the same, that is, the power frequency signal may be a common mode signal. Therefore, the power frequency signal may be suppressed using the common mode signal suppression circuit 312. In some embodiments, the common mode signal suppression circuit 312 may include a differential amplifier, an instrumentation amplifier, etc., or any combination thereof. For example, the common mode signal suppression circuit 312 may be a long tail differential amplifier. Specifically, the differential amplifier or the instrumentation amplifier may make use of the common mode properties of the initial signals of two input ends of the differential amplifier or the instrumentation amplifier to make the signals of the two input ends cancel each other to suppress the common mode signal.

In some embodiments, taking the differential amplifier as an example (such as the differential amplifier U1 in FIG. 10A), when the contact between the electrode and the human body changes (for example, one electrode in the signal acquisition circuit is in good contact, and one electrode falls off or half falls off), in other words, when the inputs of two input ends of the signal acquisition circuit are inconsistent, the input signals at the two input ends of the differential amplifier may be equivalent to changing from a common mode signal to a differential mode signal. At this time, the differential amplifier may not effectively suppress the power frequency signal. For example, for an EMG suit, as the contact between the EMG suit and the human body depends on pressure fitting, the contact between the EMG suit and the human body may be unstable. In the process of human movement, it is easy to cause dislocation, suspension (i.e., electrode falling off), etc., which may make the power frequency signal unable to be suppressed by the differential amplifier. Since human muscles, skin, electrodes, the signal processing circuit 300, etc., are connected together as a series circuit, and each link can share voltage, when the contact between an electrode and the skin changes, the input at both ends of the differential amplifier may be inconsistent. A large input impedance may have the advantage of sharing voltage in the circuit and the ability of resisting input signal fluctuation, so that when the input signal of the differential amplifier changes, it may not cause large signal fluctuation in the output signal of the differential amplifier. In the present disclosure, the advantage of sharing voltage may refer that when the contact impedance becomes larger (for example, the electrode falls off), the circuit can still share the voltage to obtain an EMG signal of sufficient strength. The ability of resisting the input signal fluctuation may refer that when the contact impedance fluctuates, the large input impedance can reduce the impact of the input signal fluctuation. Therefore, in order to suppress the power frequency signal as much as possible and obtain a strong EMG signal, the input impedance of the differential amplifier may be as large as possible to reduce the noise caused by the imbalance of the differential input ends. In some embodiments, the input impedance of the differential amplifier may be greater than or equal to 10 MΩ. For example, the input impedance of the differential amplifier may be 50 MΩ, 100 MΩ, 500 MΩ, 1 GΩ, 1.5 Go, 2 GΩ, 2.5 GΩ, 3 GΩ, 5 GΩ, 10 GΩ, etc.

In some embodiments, the first processing circuit 310 may also include a notch circuit. The notch circuit may be configured to suppress a signal of a specific frequency, such as the power frequency signal. For example, a notch point frequency of the notch circuit may be set to 50 Hz. In the present disclosure, the notch point frequency of the notch circuit may refer to a resonant frequency of the notch circuit. In some embodiments, in order to make the notch circuit have a high-quality factor (i.e., Q value) as much as possible, the notch circuit may include a dual-T active notch circuit with a high Q value (such as the notch circuit 1214 in FIG. 12A). In some embodiments, positive feedback may be introduced and/or one or more parameter values of the notch circuit may be adjusted so that a half width of a notch valley of the notch circuit may be less than a half width threshold, thereby achieving a higher quality factor Q and improving the Q value and the notch capability of the notch circuit. For example, by adjusting values and/or accuracy of resistors, capacitors, etc., in the notch circuit, the half-width of the notch valley may be within the half-width threshold. In some embodiments, the half-width threshold may be 5 Hz, 4 Hz, 3 Hz, 1 Hz, 0.5 Hz, etc.

In some embodiments, since a multiplication effect of the MA signal and the power frequency signal may generate an interference noise with a frequency of, for example, 50 Hz±2 Hz, it is necessary to broaden the half-height width of the notch circuit. In this case, the notch circuit may include a cascaded notch circuit.

Figure 3B:
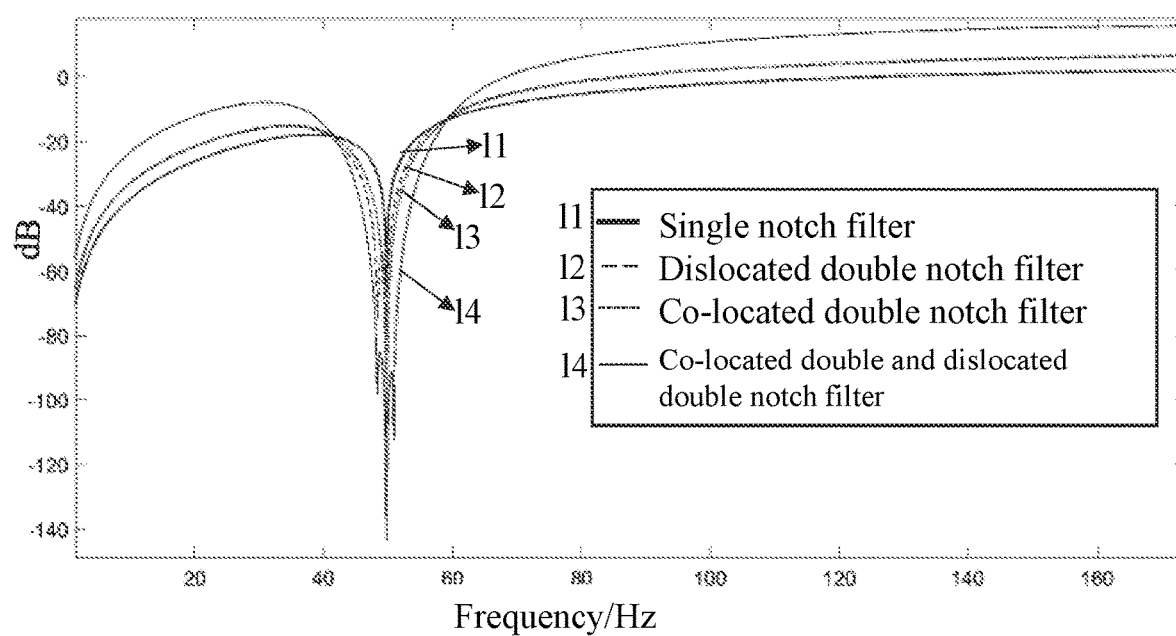
FIG. 3B is a frequency response curve diagram of various cascaded notch circuits according to some embodiments of the present disclosure.

FIG. 3B is a frequency response curve diagram of various cascaded notch circuits according to some embodiments of the present disclosure. As shown in FIG. 3B, curve I1 represents a frequency response curve of a dual-T active notch circuit. Curve I2 represents a frequency response curve of a dislocated double notch circuit. Curve I3 represents a frequency response curve of a co-located double notch circuit. Curve I4 represents a frequency response curve of a co-located double and dislocated double notch circuit. In the present disclosure, the dislocated double notch circuit may refer to a circuit in which two dual-T active notch circuits are connected in series, wherein a notch point frequency of one dual-T active notch circuit may be set as a first frequency (e.g., 48.5 Hz), and a notch point frequency of the other dual-T active notch circuit may be set as a second frequency (e.g., 50 Hz) different from the first frequency. In some embodiments, the first frequency and the second frequency may be located near a specific frequency, and a frequency difference between the first frequency and the second frequency may be within 4 Hz, 3 Hz, 2 Hz, or 1 Hz. The co-located double notch circuit may refer to a circuit in which two dual-T active notch circuits whose notch frequencies are both at a specific frequency point (such as 50 Hz) are connected in series. The co-located double and dislocated double notch circuit may refer to a circuit in which four dual-T active notch circuits are connected in series, wherein the notch point frequencies may be respectively set to, for example, 48.5 Hz, 50 Hz, 50 Hz, and 51.5 Hz. It can be seen from FIG. 3B that the frequency response (i.e., the curve I4) of the co-located double and dislocated double notch circuit has its unique advantages, such as a deeper notch capability and ensuring that its half-height width is controllable and does not affect a signal in the non-target notch area. In practical applications, an appropriate cascaded notch circuit may be selected according to the frequency value of the signal to be filtered and its intensity distribution. For example, any series of co-located and/or dislocated notch circuits may be freely cascaded according to actual needs to achieve the purpose.

In some embodiments, after the initial signal is processed by the common mode signal suppression circuit 312 and/or the notch circuit, it may be found that the first processed signal also includes many power frequency harmonic signals. For example, the initial signal may be an EMG signal acquired when the human body wears an EMG suit and performs large-scale shrugging, hand raising, or other actions. After being processed by the common mode signal suppression circuit 312 and/or the notch circuit, the initial signal may also contain the power frequency harmonic signal, especially the power frequency odd harmonic signal. In some embodiments of the present disclosure, in order to suppress the power frequency harmonic signal, the notch circuit may also include a multi-cascaded notch circuit. Specifically, the multi-cascaded notch circuit may include at least two cascaded notch sub-circuits. The at least two cascaded notch sub-circuits may be connected in series. The cascaded notch sub-circuits may have different notch point frequencies. For example, the notch point frequencies of the cascaded notch sub-circuits may be set to 50 Hz, 100 Hz, 150 Hz, 200 Hz, 250 Hz, etc. It should be pointed out that the multi-cascaded notch circuit may suppress the power frequency signal and the power frequency harmonic signal(s), but each power frequency harmonic signal may require at least one notch circuit.

In some embodiments, in order to save costs, a low-pass filter circuit 314 may be set in the signal processing circuit 300 to directly filter the power frequency harmonic signals of a relatively high-frequency band according to a commonness of the EMG signal (that is, an EMG signal with a target frequency band of 20 Hz-140 Hz may meet analysis requirements). In some embodiments, the signal processing circuit 300 may include one or more low-pass filter circuits 314. The low-pass filter circuit 314 may attenuate signals above an upper cut-off frequency of the low-pass filter circuit 314. In the present disclosure, the upper cut-off frequency of the low-pass filter circuit may refer to a frequency corresponding to a position where a gain of the low-pass filter circuit drops a first special strength value relative to a low-frequency passband. In some embodiments, the first special strength value may be greater than or equal to 10 dB, for example, 15 dB, 20 dB, 30 dB, 40 dB, or the like. In some embodiments, the upper cut-off frequency may be in a frequency range of 100 Hz to 1000 Hz. In some embodiments, the upper cut-off frequency may be in a frequency range of 100 Hz to 800 Hz. In some embodiments, the upper cut-off frequency may be in a frequency range of 100 Hz to 600 Hz. In some embodiments, the upper cut-off frequency may be in a frequency range of 100 Hz to 400 Hz. In some embodiments, the upper cut-off frequency may be in a frequency range of 120 Hz to 400 Hz. In some embodiments, the upper cut-off frequency may be in a frequency range of 140 Hz to 400 Hz. Specifically, the upper cut-off frequency may be 900 Hz, 700 Hz, 500 Hz, 300 Hz, 250 Hz, 200 Hz, 150 Hz, 140 Hz, 130 Hz, 120 Hz, 110 Hz, etc. In some embodiments, when the target frequency band is 20 Hz-140 Hz, the upper cut-off frequency may be higher than a high-frequency point of the target frequency band, for example, 140 Hz, 150 Hz, etc. In some embodiments, since the aliasing noise is a mixture of other noise signals (for example, the power frequency harmonic signal and white noise), and the aliasing noise is mainly located in the high-frequency band (for example, higher than 500 Hz), when the upper cut-off frequency of the low-pass filter circuit 314 is set relatively low (for example, 140 Hz), the low-pass filter circuit 314 may filter the aliasing noise while filtering the high-order power frequency harmonic signal(s). Since an intensity of the white noise is positively correlated with the signal bandwidth, the white noise may also be reduced relatively.

Figure 12A:
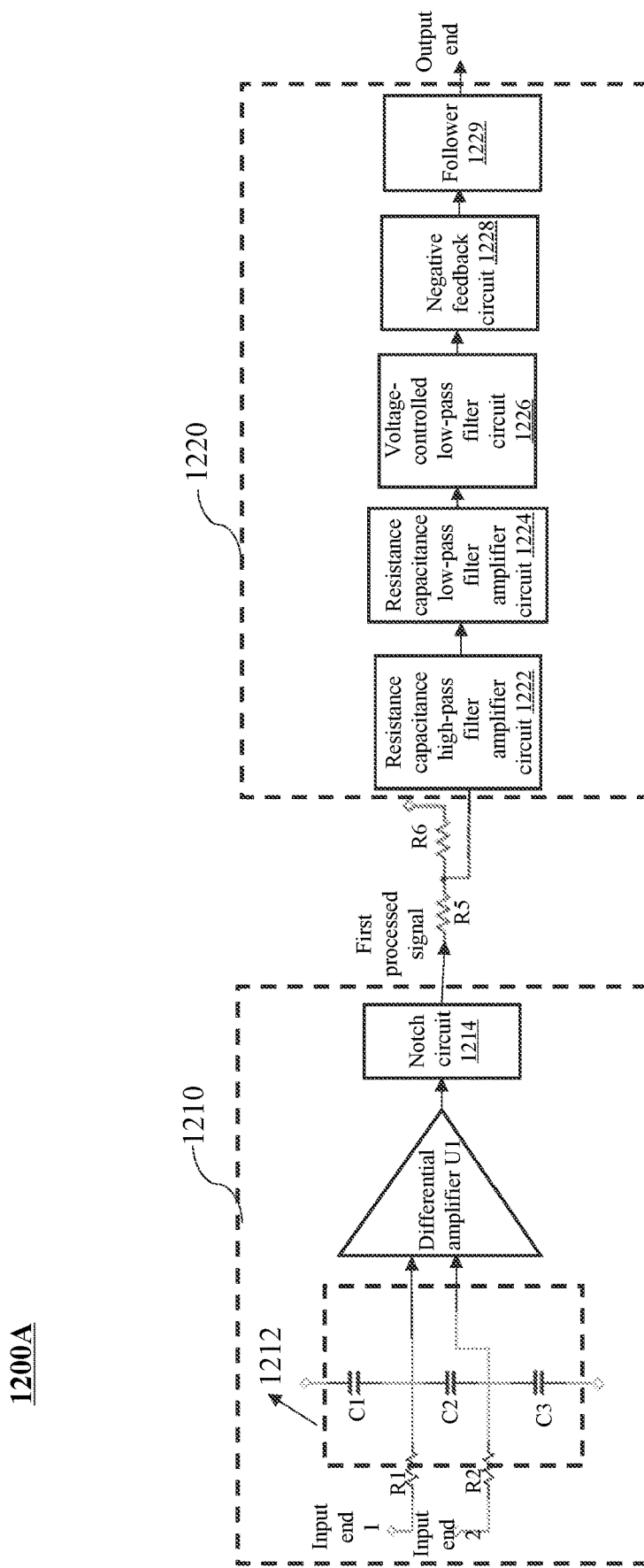
FIG. 12A is a schematic circuit diagram of an exemplary signal processing circuit according to some embodiments of the present disclosure.
Figure 12B:
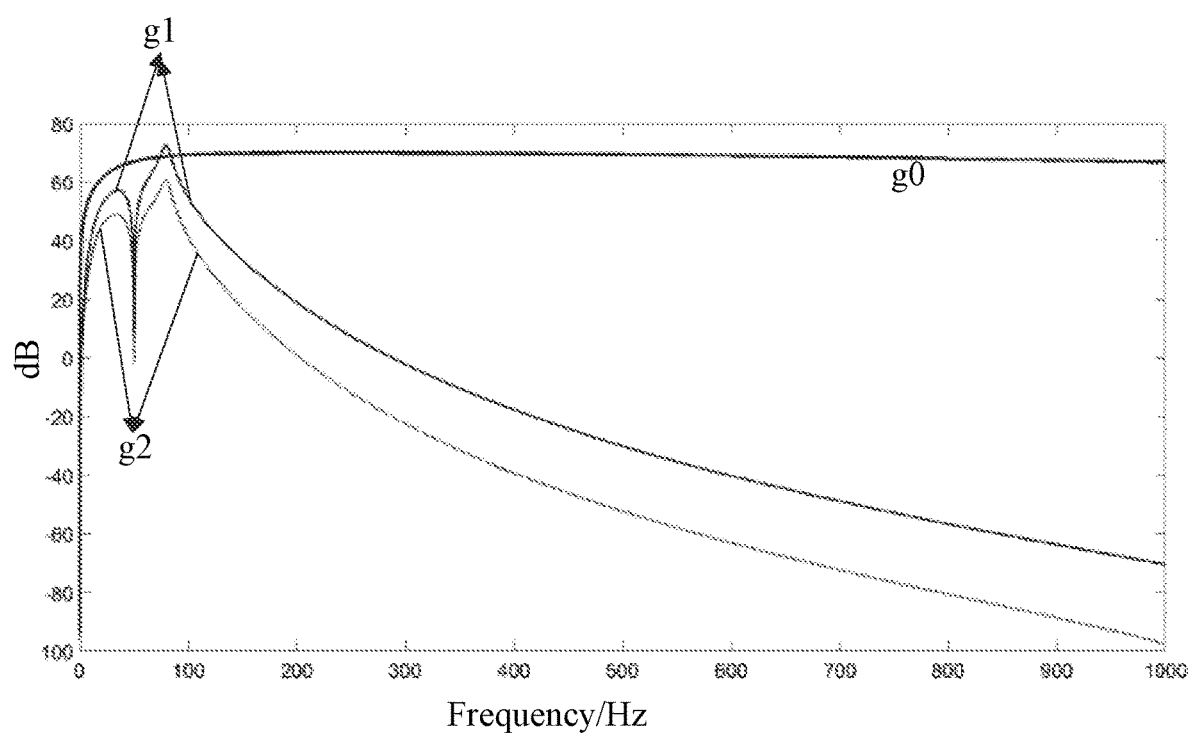
FIG. 12B illustrates a frequency response curve when a frequency response peak of the signal processing circuit in FIG. 12A is 80 Hz
Figure 12C:
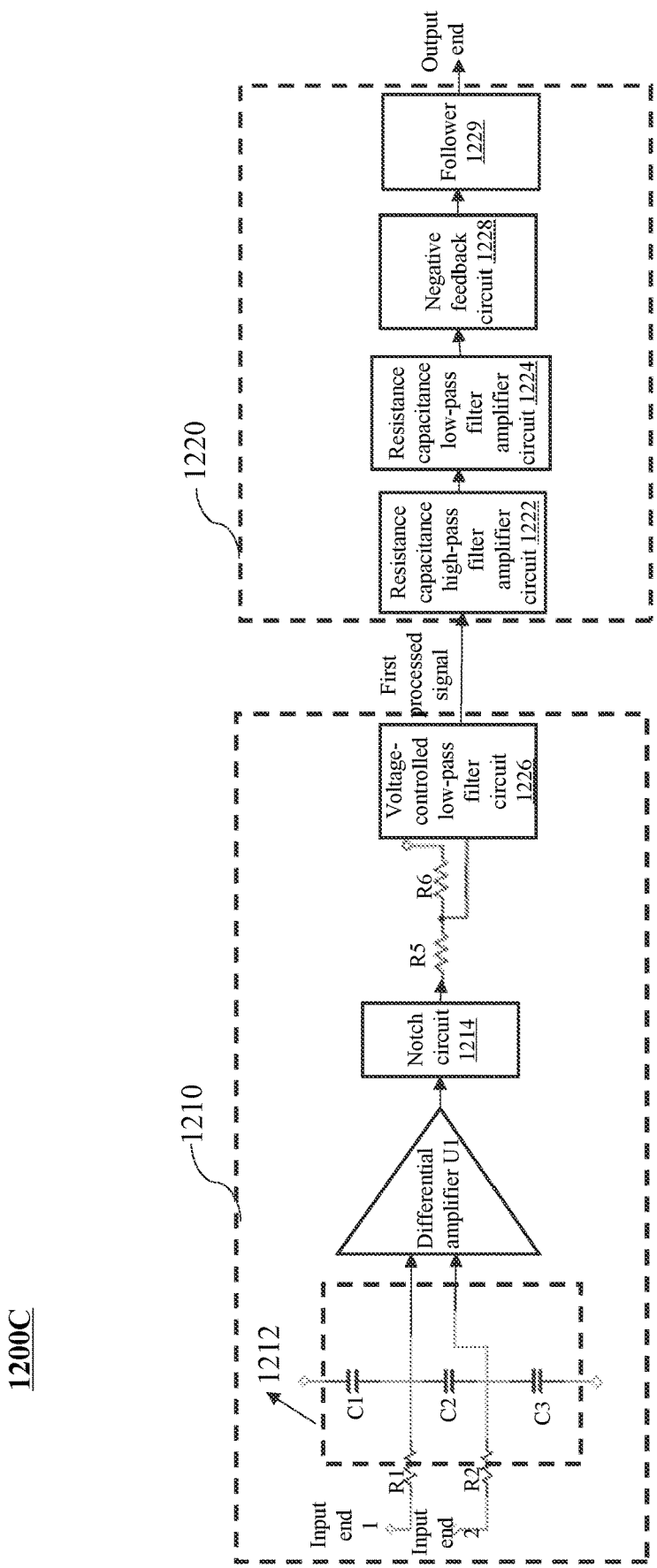
FIG. 12C is a schematic circuit diagram of an exemplary signal processing circuit according to some embodiments of the present disclosure.

In some embodiments, the low-pass filter circuit 314 may be set at any position in the signal processing circuit 300, and there is no limitation here, as long as the low-pass filter circuit 314 can perform low-pass filtering on the signal. For example, the low-pass filter circuit 314 may be provided in the first processing circuit 310. Specifically, the low-pass filter circuit(s) 314 may be set at the input end(s) of the differential amplifier. As shown in FIG. 12C, a low-pass filter consisting of a resistor R1 and a capacitor C1, and a low-pass filter consisting of a resistor R2 and a capacitor C3 may be set at the input ends of a differential amplifier U1. As another example, the low-pass filter circuit(s) 314 may also be provided in the second processing circuit 320. Specifically, the low-pass filter circuit(s) 314 may be provided at the input end(s) of the amplifier circuit in the second processing circuit 320. As shown in FIG. 12C, the second processing circuit 1220 may also include a resistance capacitance low-pass filter amplifier circuit 1224 containing a low-pass filter. In some embodiments, the low-pass filter circuit(s) 314 may include a first order low-pass filter circuit, a second order low-pass filter circuit, a high-order filter circuit (a filter circuit higher than the second order, such as a third order low-pass filter circuit), or any combination thereof. More descriptions of the low-pass filter circuit may be found elsewhere in the present disclosure (for example, FIGS. 4A to 4C and the descriptions thereof).

In some embodiments, in order to make full use of resources and use as few electronic devices as possible to more effectively suppress high-frequency signals (i.e., signals higher than the upper cut-off frequency), the low-pass filter circuit 314 may include a low-pass filter set as a bridge circuit structure (also referred to as a bridge low-pass filter circuit). For example, as shown in FIG. 12A, only a capacitor C2 needs to be added between the two input ends of the differential amplifier U1, the low-pass filter circuit may be designed as a bridge circuit structure (the circuit in dotted line box 1212). It should be known that when there is an RF signal in the initial signal, the RF signal may reach the two input ends of the differential amplifier U1 through the capacitor C2, thus RF signal can be suppressed. Therefore, the bridge low-pass filter circuit may further suppress the RF signal. In addition, the resistor R1, the resistor R2, and the capacitor C2 may also form a first-order low-pass filter, which helps narrow the transition band of the low-pass filter. In some embodiments, when the bridge low-pass filter is set at the input end(s) of the differential amplifier, the bridge low-pass filter and the differential amplifier may be collectively referred to as a bridge low-pass filter amplifier circuit. In some embodiments, the signal processing circuit 300 may not include the bridge low-pass filter circuit. For more descriptions of the bridge low-pass filter amplifier circuit, please refer to other parts of the present disclosure (for example, FIGS. 5A-5C and the descriptions thereof).

The motion artifact may refer to the noise caused by motion. The movement of different objects (e.g., pectoralis major, biceps brachii, etc.) may cause different MAs. In some embodiments, the MA may include baseline drift, burrs, or the like. For example, when the movement causes a fluctuation in the electric potential of the stratum corneum at both ends of the signal acquisition circuit, the baseline drift may be introduced. Generally, the frequency of the MA may be in a lower frequency range, for example, 0 Hz-20 Hz. The strength of the MA may be in a range of 0 mV to 40 mV. In some embodiments of the present disclosure, since the frequency band where the MA is located is outside the target frequency band, the MA may be processed by constructing a high-pass filter circuit 316. In some embodiments, since the baseline drift has a limit value, the baseline drift may also be solved by reducing the gain of the signal processing circuit 300 (for example, the second processing circuit 320) to the target signal, and/or selecting a control chip with a high-precision ADC channel, and/or selecting a resistor to adjust the reference potential. For example, when the target signal is transmitted to the second processing circuit 320, the second processing circuit 320 may amplify the target signal. In order to solve the problem of baseline drift, an amplification factor of the second processing circuit 320 for the target signal may be appropriately reduced, so that the amplified signal may not be distorted. As another example, when the baseline drift makes the signal close to an upper limit of saturation voltage, the reference potential may be controlled to decrease by program control; on the contrary, when the baseline drift makes the signal close to a lower limit of voltage, the reference potential may be controlled to increase by program control. In some embodiments, the frequency range of the MA may be very wide, for example, burrs may exist in the range of 0-1000 Hz. In this case, the amplitude and frequency of the signal may be used for processing.

In some embodiments, the signal processing circuit 300 may include one or more high-pass filter circuits 316. The high-pass filter circuit 316 may attenuate signals below a lower cut-off frequency of the high-pass filter circuit 316. In the present disclosure, the lower cut-off frequency of the high-pass filter circuit may refer to a frequency corresponding to a position where a gain decreases by a second special strength value relative to a high-frequency passband. In some embodiments, the second special strength value may be greater than or equal to 10 dB, for example, 15 dB, 20 dB, 30 dB, 40 dB, and the like. In some embodiments, the second special strength value may be the same as or different from the first special strength value. In some embodiments, the lower cut-off frequency may be in a frequency range of 5 Hz to 200 Hz. In some embodiments, the lower cut-off frequency may be in a frequency range of 7 Hz to 180 Hz. In some embodiments, the lower cut-off frequency may be in a frequency range of 10 Hz to 160 Hz. In some embodiments, the lower cut-off frequency may be in a frequency range of 10 Hz to 100 Hz. In some embodiments, the lower cut-off frequency may be in a frequency range of 10 Hz to 80 Hz. In some embodiments, the lower cut-off frequency may be in a frequency range of 10 Hz to 60 Hz. In some embodiments, the lower cut-off frequency may be in a frequency range of 10 Hz to 40 Hz. In some embodiments, the lower cut-off frequency may be in a frequency range of 10 Hz to 20 Hz. Specifically, the lower cut-off frequency may be 190 Hz, 150 Hz, 100 Hz, 70 Hz, 50 Hz, 30 Hz, 20 Hz, 17 Hz, 15 Hz, 13 Hz, 12 Hz, 10 Hz, 5 Hz, etc.

In some embodiments, the lower cut-off frequency may vary depending on whether there is a notch circuit for the power frequency signal in the signal processing circuit 300. When there is a notch circuit with a notch point frequency of the power frequency, since the interference of the power frequency signal may be effectively suppressed by the notch circuit, at this time, the lower cut-off frequency of the high-pass filter circuit 316 may be lower than the lower cut-off frequency when there is no notch circuit. For example, if the first processing circuit 310 includes a notch circuit, the lower cut-off frequency may be in a frequency range of 10 Hz to 40 Hz. Specifically, if the first processing circuit 310 includes a notch circuit, the lower cut-off frequency may be 35 Hz, 30 Hz, 25 Hz, 20 Hz, 10 Hz, etc. As another example, if the first processing circuit 310 does not include a notch circuit, the lower cut-off frequency may be within a frequency range of 10 Hz-160 Hz. Specifically, if the first processing circuit 310 does not include a notch circuit, the lower cut-off frequency may be 80 Hz, 60 Hz, 50 Hz, 20 Hz, etc. In some embodiments, the lower cut-off frequency of the high-pass filter circuit 316 may be set according to the target frequency band. For example, if the target frequency band is 20 Hz-140 Hz, the lower cut-off frequency may be set to 20 Hz. If the target frequency band is 5 Hz-200 Hz, the lower cut-off frequency may be set to 5 Hz.

In some embodiments, the high-pass filter circuit 316 may be set at any position in the signal processing circuit 300, which is no limited here, as long as the high-pass filter circuit 316 may perform high-pass filtering on the signal. For example, the high-pass filter circuit 316 may be provided in the first processing circuit 310. Specifically, for example, in the signal processing circuit 1000 shown in FIG. 10A, the output end of the differential amplifier U1 in the first processing circuit 1010 may be provided with a high-pass filter 1014. As another example, the high-pass filter circuit 316 may also be arranged in the second processing circuit 320. Specifically, for example, in the signal processing circuit 1200A shown in FIG. 12A, the second processing circuit 1220 may be provided with a resistance capacitance high-pass filter amplifier circuit 1222 including a high-pass filter. In some embodiments, the high-pass filter circuit 316 may include a first order high-pass filter circuit, a second order high-pass filter circuit, a third order high-pass filter circuit, or any combination thereof. More descriptions of the high-pass filter circuit may be found elsewhere in the present disclosure (for example, FIGS. 9A-9C and the descriptions thereof).

In some embodiments, in order to make a frequency response passband of the signal processing circuit 300 more flat (that is, the signal fluctuation within the bandwidth does not exceed a certain value, such as 10 dB, 20 dB, etc.), the signal processing circuit 300 may also include a voltage-controlled low-pass filter circuit. The voltage-controlled low-pass filter circuit may include a voltage-controlled peak (e.g., the peak 712 of curve d2 shown in FIG. 7B). The voltage-controlled low-pass filter circuit may be configured to provide a gain near the target frequency, and combined with the low-pass filter circuit 314 to compensate the attenuation of the low-pass filter circuit 314, so as to obtain a flatter frequency response passband. In this specification, being near the target frequency may refer to being within a certain range (for example, 10 Hz, 20 Hz, etc.) from a certain frequency in the target frequency band. In some embodiments, by setting parameters of the voltage-controlled low-pass filter circuit and/or parameters of the voltage-controlled peak of the voltage-controlled low-pass filter circuit, the frequency response passband may also be made to have a relatively high peak at a specific frequency point (that is, a relatively large gain may be provided at the specific frequency position). For example, the cut-off frequency of the voltage-controlled low-pass filter circuit and/or the height, width, position, etc., of the voltage-controlled peak of the voltage-controlled low-pass filter circuit may be adjusted by adjusting parameters of resistances and capacitances in the voltage-controlled low-pass filter circuit, so that the frequency response passband of the signal processing circuit 300 can have the highest strength at, for example, 80 Hz. In some embodiments, a drop rate of the voltage-controlled low-pass filter circuit may be greater than 20 dB/decade. In some embodiments, the drop rate of the voltage-controlled low-pass filter circuit may be greater than 30 dB/decade. In some embodiments, the drop rate of the voltage-controlled low-pass filter circuit may be greater than 40 dB/decade. In some embodiments, the drop rate of the voltage-controlled low-pass filter circuit may be greater than 60 dB/decade. In some embodiments, the drop rate of the voltage-controlled low-pass filter circuit may be greater than 80 dB/decade. Specifically, the drop rate of the voltage-controlled low-pass filter circuit may be 25 dB/decade, 35 dB/decade, 45 dB/decade, 55 dB/decade, 65 dB/decade, 75 dB/decade, etc.

In some embodiments, the voltage-controlled low-pass filter circuit may be set at any position in the signal processing circuit 300, which is not limited here, as long as the voltage-controlled low-pass filter circuit can regulate the signal. For example, the voltage-controlled low-pass filter circuit may be provided in the first processing circuit 310. Specifically, in the signal processing circuit 1200C shown in FIG. 12C, the voltage-controlled low-pass filter circuit 1226 may be set after the notch circuit 1214 in the first processing circuit 1210. As another example, the voltage-controlled low-pass filter circuit may also be set in the second processing circuit 320. Specifically, in the signal processing circuit 1200A shown in FIG. 12A, the voltage-controlled low-pass filter circuit 1226 may be set before the follower 1229 in the second processing circuit 1220. More descriptions about the voltage-controlled low-pass filter circuit may be found elsewhere in the present disclosure (for example, FIGS. 7A-7B and the descriptions thereof).

Figure 6A:
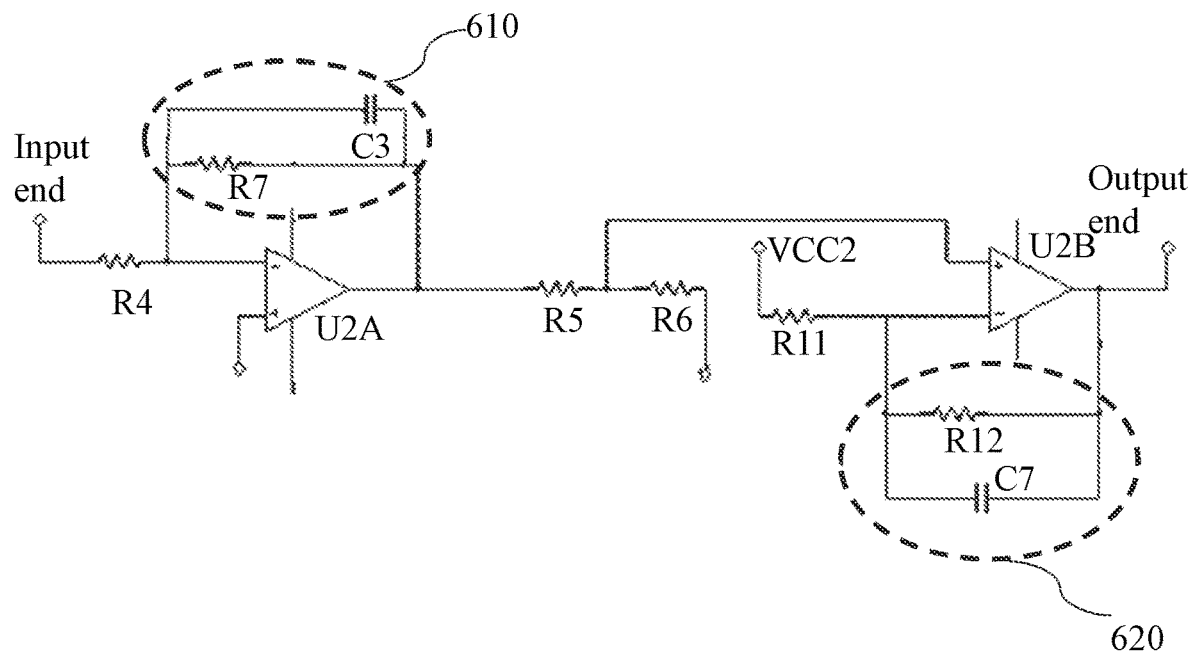
FIG. 6A is a schematic structural diagram of a resistance capacitance low-pass filter circuit according to some embodiments of the present disclosure.

The second processing circuit 320 may be configured to amplify the first processed signal. The second processing circuit 320 may include an amplifier circuit (e.g., an amplifier). In some embodiments, a resistance of a feedback network in the amplifier circuit may be replaced by a resistance and a capacitor connected in parallel, so that the formed circuit may be called a resistance capacitance amplifier circuit, and a feedback network of the resistance capacitance amplifier circuit may be called a resistance capacitance feedback network. For example, as shown in FIG. 6A, the amplifier U2B and the resistor R12 and the capacitor C7 in the feedback network of the amplifier U2B may form a resistance capacitance amplifier circuit, and the resistor R12 and the capacitor C7 connected in parallel may be called a resistance capacitance feedback network. It should be known that due to an impedance of a capacitor changes with the frequency of an AC signal, so the gain of the resistance capacitance amplifier circuit may also change with the frequency of a signal. Therefore, the gain multiple of the second processing circuit 320 to the first processed signal may vary with the frequency of the first processed signal. Specifically, taking the feedback network 620 (also known as the resistance capacitance feedback network) of the amplifier U2B in FIG. 6A as an example, since there is a capacitor C7 on the feedback network 620 of the amplifier U2B, according to the characteristic that the impedance of the capacitor changes with the frequency of the AC signal, the higher the signal frequency, the more current signals may directly flow from the capacitor C7 to the output end of the amplifier U2B. When the signal frequency is large enough, the effect of the resistor R12 may be weakened. At this time, the current signal may flow directly from the capacitor C7 to the output end of the amplifier U2B, resulting in the circuit gain attenuation or even no gain. In other words, compared with a high-frequency signal, the low-frequency signal may be easier to be amplified through the amplifier U2B. Finally, it may show that the resistance capacitance amplifier circuit has the effect of the low-pass filter circuit. Therefore, in the present disclosure, by building a resistance capacitance feedback network in the amplifier circuit, a better high-frequency and low-frequency suppression effect may be realized using as few amplifiers as possible, which may reduce a production cost of the circuit. In some embodiments, the resistance capacitance amplifier circuit may also be referred to as the resistance capacitance low-pass filter circuit. For more descriptions of the resistance capacitance low-pass filter circuit, please refer to other parts of the present disclosure (for example, FIGS. 6A-6B and the descriptions thereof). In some embodiments, when the resistance capacitance amplifier circuit is connected with a high-pass filter circuit or a low-pass filter circuit, the combined circuit may also be called a resistance capacitance high-pass filter circuit or a resistance capacitance low-pass filter circuit.

In some embodiments, the gain of the amplifier circuit (or the second processing circuit 320) to the signal in the target frequency band may be adjusted by adjusting values of the resistance and capacitance of the feedback network in the amplifier circuit. In some embodiments, the second processing circuit 320 may have a relatively large gain for signals within a first frequency range and a relatively small gain for signals outside the first frequency range. In other words, the second processing circuit 320 may process the first processed signal to achieve a bandpass effect. For example, the second processing circuit 320 may have a gain of more than 100 times for signals in the target frequency band (for example, 20 Hz-140 Hz), and a gain of less than 100 times for signals outside the target frequency band. The farther away from the target frequency band, the smaller the corresponding gain.

In some embodiments, the second processing circuit 320 may be configured to amplify the first processed signal by a second amplification factor. In some embodiments, the second amplification factor of the second processing circuit 320 may also refer to a total amplification factor of all amplifiers in the second processing circuit 320 to amplify the signal. In some embodiments, the second amplification factor may be 15 times, 20 times, 50 times, 100 times, 200 times, 300 times, 500 times, etc. In some embodiments, in order to make a signal of a specific frequency band (for example, a bandpass band) has a greater gain, the amplifier circuit may include a multistage amplifier circuit. In some embodiments, the second amplification factor may be related to the noise signal in the first processed signal, an ADC accuracy of the digital circuit, etc. For example, when there is a baseline drift in the first processed signal, the second amplification factor may be appropriately reduced and/or a control circuit with a higher accuracy ADC may be selected to control the baseline drift not to exceed the output capacity of the signal processing circuit 300, so that distortion may not occur.

It should be noted that since the first processing circuit 310 includes one or more amplifiers (for example, differential amplifiers), the first amplification factor of the first processing circuit 310 may refer to a total amplification factor of all amplifiers in the first processing circuit 310 to amplify the signal. In some embodiments, in order to process the noise signal in the initial signal preferentially, the first amplification factor of the first processing circuit 310 may be set to be less than 20 times. For example, the first amplification factor may be 20 times, 15 times, 10 times, 9 times, 7 times, 5 times, and so on. In some embodiments, the second amplification factor of the second processing circuit 320 may be greater than, less than, or equal to the first amplification factor of the first processing circuit 310. For example, the first amplification factor may be 20 times, and the second amplification factor may be 200 times. As another example, the first amplification factor may be 20 times, and the second amplification factor may be 15 times. As further another example, both the first amplification factor and the second amplification factor may be 20 times.

In some embodiments, according to the characteristic that the gain of the signal processing circuit 300 (for example, the second processing circuit 320) to the signal changes with the frequency, in order to suppress the power frequency signal as much as possible, a frequency response peak of the signal processing circuit 300 may be set as far away from the frequency 50 Hz of the power frequency signal as possible. For example, the frequency response peak of the signal processing circuit 300 may be set to 80 Hz, 90 Hz, 100 Hz, 110 Hz, 120 Hz, etc. Because in this case, even if the frequency response peak of the signal processing circuit 300 is at, for example, 120 Hz, the signal processing circuit 300 may have a maximum gain for the signal of 120 Hz, and a relatively small gain for the signal far away from 120 Hz, which may be equivalent to further suppressing the power frequency signal. At this time, the gain of the signal processing circuit 300 is still strong at 80 Hz-100 Hz, which meets the analysis requirements for the EMG signal. On the whole, the purpose of attenuating noise may be achieved by adjusting a peak position of the frequency response gain of the signal processing circuit 300 to make the peak position far away from the frequency of the noise to be suppressed. For example, in order to reduce an influence of a third harmonic in the power frequency harmonic signal, the frequency response peak of the signal processing circuit 300 may be set away from 150 Hz (for example, 80 Hz).

In some embodiments, the second processing circuit 320 may also include a follower. The follower may be configured to isolate an interaction between the output end of the signal processing circuit 300 and the following circuit.

In some embodiments, the signal processing circuit 300 may also include a negative feedback circuit. The negative feedback circuit may be configured to adjust the second amplification factor of the amplifier circuit. In some embodiments, the signal processing circuit 300 may also include a feedback circuit. The feedback circuit may be configured to improve or control performance indicators of the signal processing circuit 300, for example, to suppress interference, noise, and the like. More descriptions for the signal processing circuit may be found elsewhere in the present disclosure (for example, FIG. 10, FIG. 11, FIG. 12A, FIG. 12C, and the descriptions thereof).

It should be noted that the above description of the signal processing circuit 300 is merely for example and description, and does not limit the scope of the present disclosure. For those skilled in the art, various amendments and changes may be made to the signal processing circuit 300 under the guidance of the present disclosure. However, these amendments and changes are still within the scope of the present disclosure. For example, a signal processed by the signal processing circuit 300 may also be processed using a noise reduction algorithm. In some embodiments, the noise reduction algorithm may include a filtering algorithm, a spectral subtraction algorithm, an adaptive algorithm, a minimum mean square error estimation algorithm, or the like, or any combination thereof.

Figure 4A:
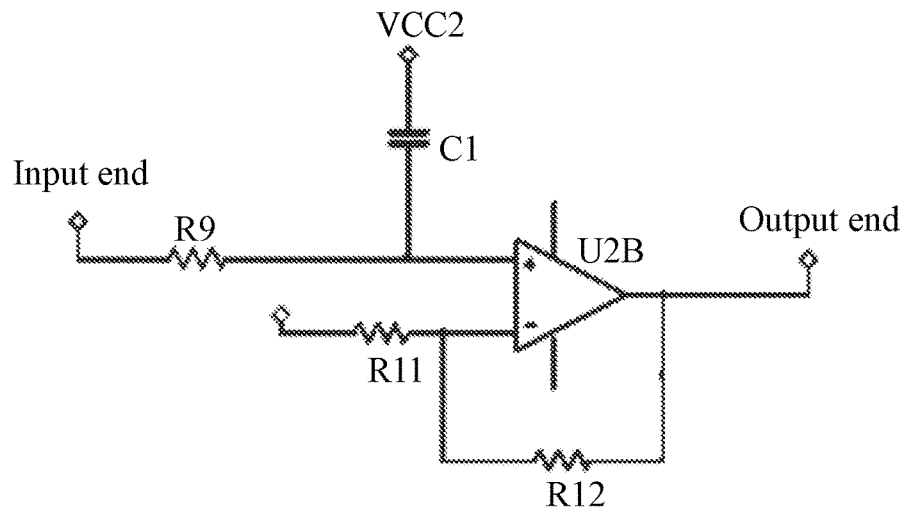
FIGS. 4A-4C are schematic structural diagrams of exemplary low-pass filter circuits according to some embodiments of the present disclosure.
Figure 4B:
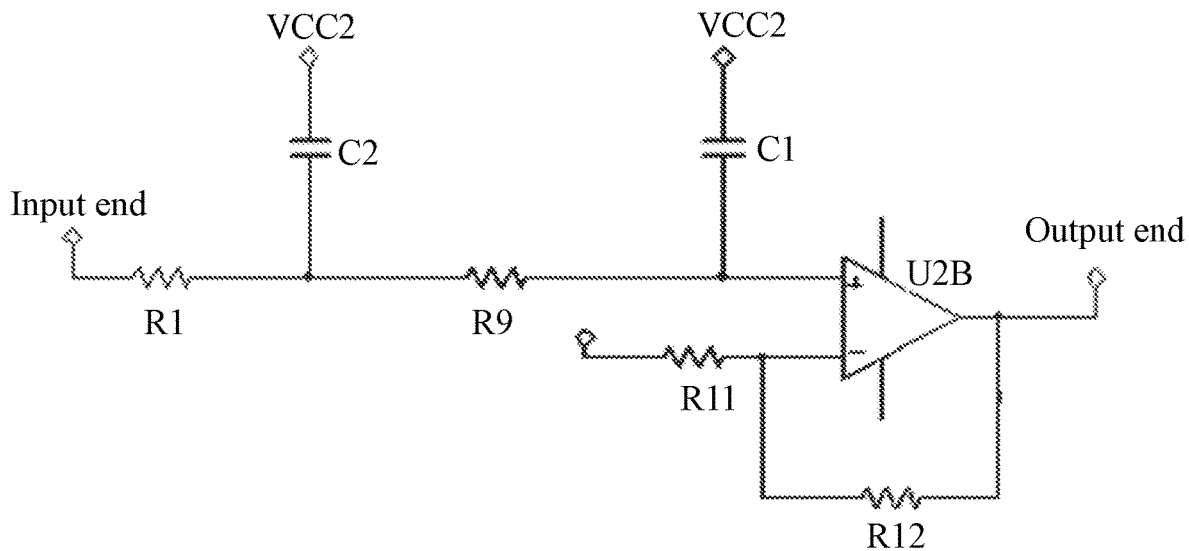
Figure 4C:
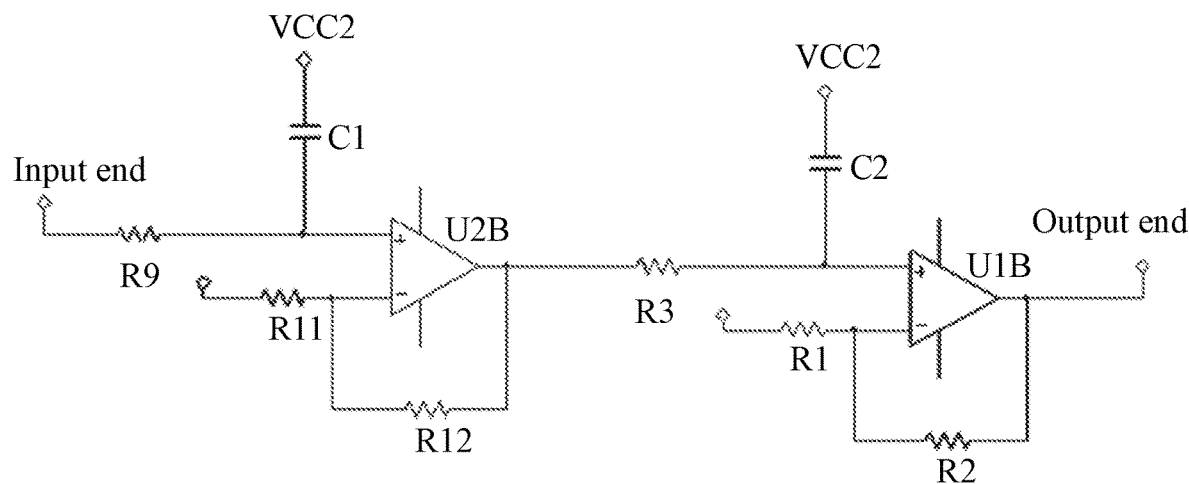
Figure 4D:
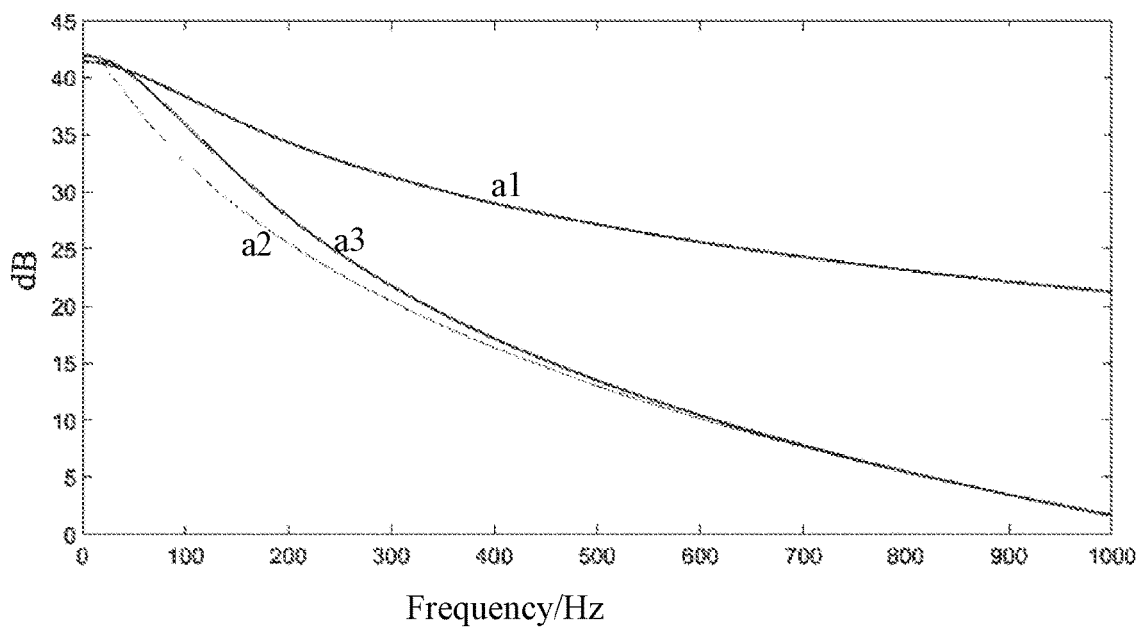
FIG. 4D is a frequency response curve diagram of the low-pass filter circuits in FIG. 4A, FIG. 4B, and FIG. 4C.

FIG. 4A, FIG. 4B, and FIG. 4C are schematic structural diagrams of exemplary low-pass filter circuits according to some embodiments of the present disclosure. FIG. 4D is a frequency response curve diagram of the low-pass filter circuits in FIG. 4A, FIG. 4B, and FIG. 4C.

As shown in FIG. 4A, the low-pass filter circuit 400A may include a first low-pass filter composed of a resistor R9 and a capacitor C1, and an amplifier U2B. The first low-pass filter may be connected to an input end of the amplifier U2B. In some embodiments, the low-pass filter circuit 400A may also be called a first-order active low-pass filter circuit.

As shown in FIG. 4B, compared with the low-pass filter circuit 400A, the low-pass filter circuit 400B may further include a second low-pass filter composed of a resistor R1 and a capacitor C2. The first low-pass filter may be directly connected with the second low-pass filter. In some embodiments, as shown in the low-pass filter circuit 400B, a second-order low-pass filter circuit formed by directly connecting the two low-pass filters may also be called a second-order cascaded low-pass filter circuit.

As shown in FIG. 4C, compared with the low-pass filter circuit 400A, the low-pass filter circuit 400C may further include a third low-pass filter composed of a resistor R3 and a capacitor C2, an amplifier U1B, the resistor R1, and the resistor R2. The third low-pass filter may be connected to an output end of the amplifier U2B and an input end of the amplifier U1B. In some embodiments, as shown in the low-pass filter circuit 400C, the second-order low-pass filter circuit formed by directly connecting two first-order active low-pass filter circuits may also be called a second-order distributed low-pass filter circuit.

As shown in FIG. 4D, the curve a1 represents a frequency response curve of a first-order active low-pass filter circuit (i.e., the low-pass filter circuit 400A). The curve a2 represents a frequency response curve of a second-order low-pass filter circuit (i.e., the low-pass filter circuit 400B). The curve a3 may represent a frequency response curve of a second-order distributed low-pass filter circuit (i.e., the low-pass filter circuit 400C). It may be seen from FIG. 4D that low-pass filter circuits with different structures may have different frequency responses. The first-order active low-pass filter circuit 400A (corresponding to the curve a1) may reach an attenuation speed of 15 dB/decade (100 Hz to 1 kHz), the second-order cascaded low-pass filter circuit 400B (corresponding to the curve a2) may reach an attenuation speed of 30 dB/decade (100 Hz to 1 kHz), and the second-order distributed low-pass filter circuit 400C (corresponding to the curve a3) may reach an attenuation speed of 34 dB/decade (100 Hz to 1 kHz).

In some embodiments, when it is desired to achieve the same suppression effect at 1 kHz, in order to retain more low-frequency signals (for example, signals within 120 Hz), a high-order (for example, second-order) filter circuit may be preferred. It should be noted that a reason for a difference between the second-order cascaded low-pass filter circuit and the second-order distributed low-pass filter circuit may be that the second order of the two-order cascaded low-pass filter circuit has an impact on the first order of the two-order cascaded low-pass filter circuit. When the current flows through the resistor of the first order, it seems to a next node that the capacitor in the first order is connected in parallel with the second order circuit, which actually increases a total capacitance value, thereby leading to the reduction of a cut-off point of the frequency response of the second-order cascaded low-pass filter circuit and filtering out more low-frequency signals.

FIG. 5A-5B are schematic structural diagrams of low-pass filter circuits according to some embodiments of the present disclosure. FIG. 5C is a frequency response curve diagram of the low-pass filter circuits in FIG. 5A and FIG. 5B.

As shown in FIGS. 5A and 5B, both the low-pass filter circuit 500A and the low-pass filter circuit 500B may include two low-pass filters (for example, a low-pass filter composed of the resistor R1 and the capacitor C8, and a low-pass filter composed of the resistor R2 and the capacitor C12) and the differential amplifier U1. A difference between the low-pass filter circuit 500A and the low-pass filter circuit 500B may be that the input end of the differential amplifier U1 in the low-pass filter circuit 500B forms a bridge circuit structure (a first node is between the resistor R1 and the capacitor C8, the second node is between the resistor R2 and the capacitor C12, and both ends of the capacitor C11 are connected to the first node and the second node, respectively) by adding the capacitor C11 (the dotted circle part). In some embodiments, the low-pass filter circuit 500A may also be called a first-order active low-pass filter circuit. The low-pass filter circuit 500B may also be called a bridge low-pass filter circuit. It should be known that when there is a RF signal in the input signal, the RF signal may reach the two input ends of the differential amplifier U1 through the capacitor C11, thereby being suppressed by the common mode suppression ability of the differential amplifier U1. Therefore, the bridge low-pass filter circuit may further suppress the RF signal. In addition, the resistor R1, the resistor R2, and the capacitor C11 may also form a first-order low-pass filter, which may help narrow a filter transition band.

As shown in FIG. 5C, the curve b1 represents a frequency response curve of the first-order active low-pass filter circuit (i.e., the low-pass filter circuit 500A). The curve b2 represents a frequency response curve of the bridge low-pass filter circuit (i.e., the low-pass filter circuit 500B). It may be seen from FIG. 5C that by adding the capacitor C11 between the input ends of the differential amplifier U1 to build the bridge circuit structure, the suppression effect of the low-pass filter circuit on a high frequency may be enhanced. For example, at 1 kHz, a frequency response intensity of the low-pass filter circuit 500A is 6 dB stronger than a frequency response intensity of the low-pass filter circuit 500B. It should be understood that the principle of the bridge circuit structure may be interpreted that an additional capacitance (i.e., the capacitor C11) may enable AC signals of some frequencies to pass through the additional capacitance from one input channel to the other input channel, and finally to reach the differential amplifier U1, and thus achieves the attenuation effect after the common mode suppression. Adjusting capacitance values of the additional capacitance may control the frequency of the AC signal that may pass through the capacitance.

Figure 6B:
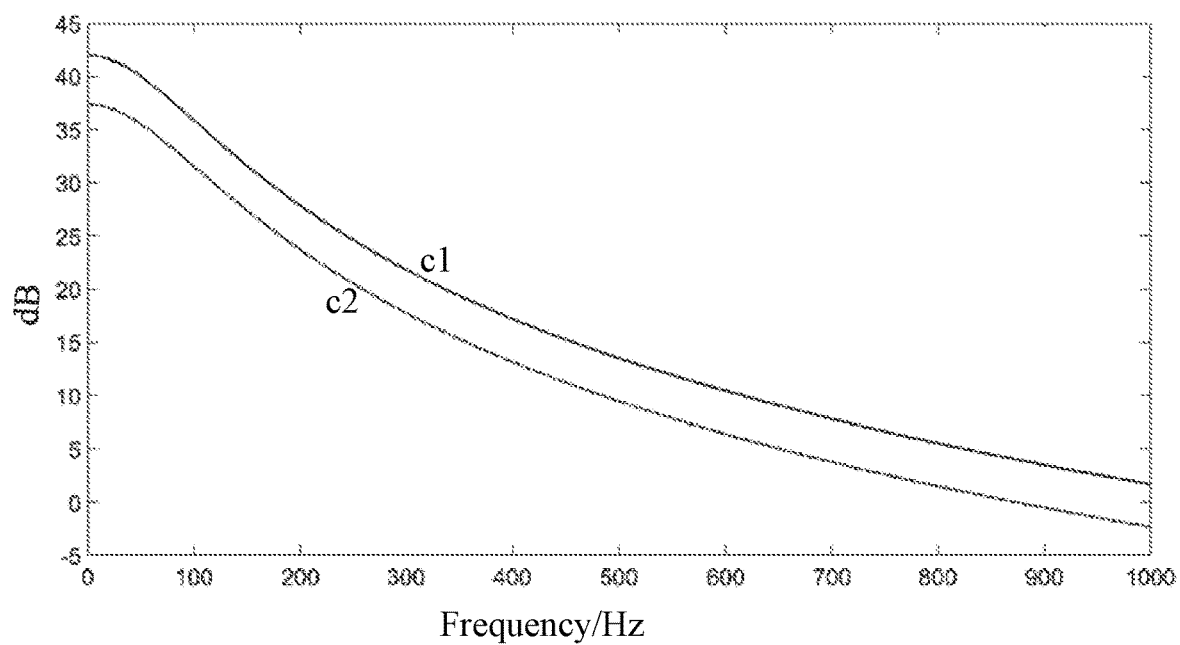
FIG. 6B is a frequency response curve diagram of a second-order distributed low-pass filter circuit and the resistance capacitance low-pass filter circuit in FIG. 6A.

FIG. 6A is a schematic structural diagram of a resistance capacitance low-pass filter circuit according to some embodiments of the present disclosure. FIG. 6B is a frequency response curve diagram of a second-order distributed low-pass filter circuit and the resistance capacitance low-pass filter circuit in FIG. 6A.

As shown in FIG. 6A, the resistance capacitance low-pass filter circuit 600 may include a second-order distributed resistance capacitance low-pass filter circuit, which may be different from the second-order distributed low-pass filter circuit (for example, the second-order distributed low-pass filter circuit 400C) in that the capacitor in the low-pass filter in the second-order distributed low-pass filter circuit is removed; in addition, the resistor in the feedback network of the second-order distributed low-pass filter circuit is replaced by the resistor and the capacitor connected in parallel, that is, the resistance capacitance feedback network is constructed. For example, in FIG. 6A, if a capacitor connected to a reference potential/ground is connected after the resistor R4 and a resistor is connected in series at the output end of the U2A, and a capacitor connected to the reference potential/ground is connected, and the capacitors in the resistance capacitance feedback networks 610 and 620 are removed, the resulting circuit is a second-order distributed low-pass filter circuit. In some embodiments, the second-order distributed resistance capacitance low-pass filter circuit may also be called a second-order distributed resistance capacitance amplifier circuit.

It should be known that an impedance of a capacitor may change with the frequency of an AC signal, so a gain of the second-order distributed resistance capacitance low-pass filter circuit may also change with the frequency of the signal. Specifically, taking the resistance capacitance feedback network 620 of the amplifier U2B in FIG. 6A as an example, since there is a capacitor C7 on the resistance capacitance feedback network 620 of the amplifier U2B, according to the characteristic that the impedance of the capacitor changes with the frequency of the AC signal, with an increase of the signal frequency, a current signal that directly flows from the capacitor C7 to the output end of the amplifier U2B may increase gradually. When the signal frequency is large enough, the effect of the resistor R12 may be weakened. At this time, the current signal may flow directly from the capacitor C7 to the output end of the amplifier U2B, resulting in the circuit gain attenuation or even no gain. Therefore, the gain of the amplifier U2B to the signal within the target frequency band may be adjusted by adjusting the values of the resistor R12 and the capacitor C7. In the same way, the values of the resistor R7 and the capacitor C3 may be adjusted to adjust the gain of the amplifier U2A to the signal within the target frequency band.

As shown in FIG. 6B, the curve c1 represents a frequency response curve of the second-order distributed low-pass filter circuit (for example, the low-pass filter circuit 400C). The curve c2 represents a frequency response curve of the second-order distributed resistance capacitance low-pass filter circuit (i.e., the low-pass filter circuit 600). It may be seen from FIG. 6B that the second-order distributed resistance capacitance low-pass filter circuit (corresponding to the curve c2) and the second-order distributed low-pass filter circuit (corresponding to the curve c1) have frequency responses with the same change trend. The second-order distributed resistance capacitance low-pass filter circuit may be compatible with the second-order distributed low-pass filter circuit. In some embodiments, in order not to increase the number of amplifiers additionally and to have a strong ability to suppress high frequencies, the second-order distributed resistance capacitance low-pass filter circuit may be preferably selected.

Figure 7A:
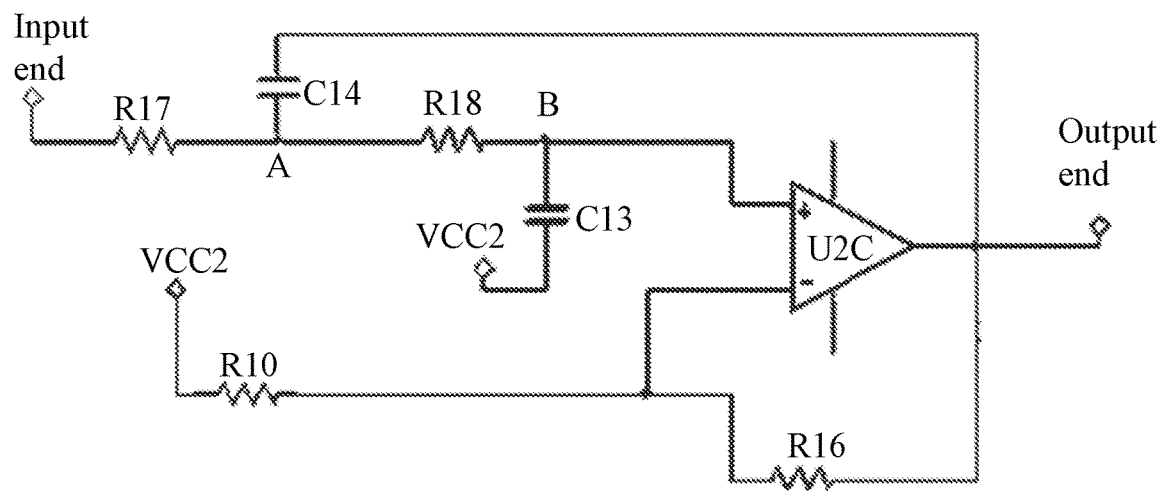
FIG. 7A is a schematic structural diagram of a voltage-controlled low-pass filter circuit according to some embodiments of the present disclosure.
Figure 7B:
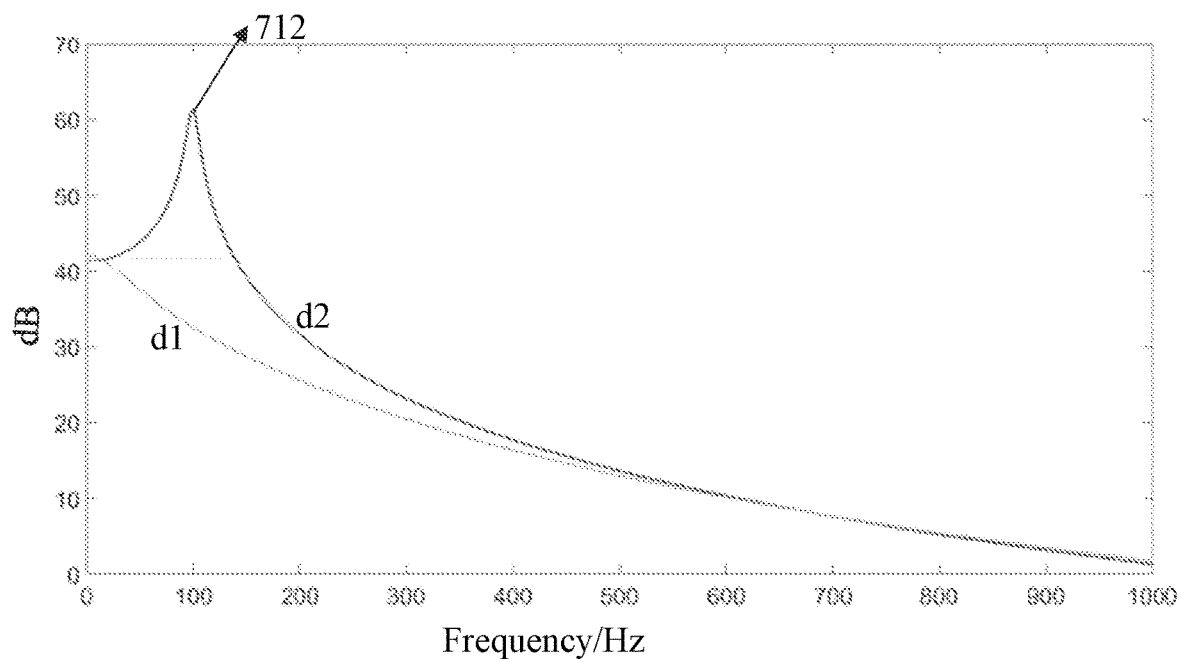
FIG. 7B is a frequency response curve diagram of a second-order low-pass filter circuit and the voltage-controlled low-pass filter circuit in FIG. 7A.

FIG. 7A is a schematic structural diagram of a voltage-controlled low-pass filter circuit according to some embodiments of the present disclosure. FIG. 7B is a frequency response curve diagram of a second-order low-pass filter circuit and the voltage-controlled low-pass filter circuit in FIG. 7A.

As shown in FIG. 7A, the voltage-controlled low-pass filter circuit 700 may have a structure similar to the second-order low-pass filter circuit 400B. A difference between the voltage-controlled low-pass filter circuit 700 and the second-order low-pass filter circuit 400B may be that a capacitor (i.e., the capacitor C14) of a first-order low-pass filter in the voltage-controlled low-pass filter circuit 700 is directly connected with the output end of the amplifier in the voltage-controlled low-pass filter circuit 700 to form a feedback loop of an output voltage. In some embodiments, the voltage-controlled low-pass filter circuit 700 may also be called a voltage-controlled voltage source second-order low-pass filter circuit.

By designing the voltage-controlled low-pass filter circuit 700, the response of a certain frequency may reach a relatively large value, so that the frequency response curve of the voltage-controlled low-pass filter circuit 700 may include a convex peak. As shown in FIG. 7B, the curve d1 represents a frequency response curve of the second-order cascaded low-pass filter circuit. The curve d2 represents a frequency response curve of the voltage-controlled voltage source second-order low-pass filter circuit (that is, the voltage-controlled low-pass filter circuit 700).

This is because when the frequency is too low, the capacitor C13 and the capacitor C14 in FIG. 7A may be equivalent to being in a disconnected state, and the capacitor C14 may have no feedback effect. When the frequency is gradually increased, the feedback effect of the capacitor C14 may gradually take effect. However, when the frequency is particularly high, the capacitor C13 may lead a large number of input signals and the feedback signals into the virtual ground, which may reduce the output. Therefore, different values of the capacitors C13 and C14 may be controlled to design feedback and retain signals of high-frequency. In some embodiments, a quantitative calculation of specific values of the capacitors C13 and C14 may depend on a transfer function.

In FIG. 7A, R17=R18=R, C13=C14=C, the input signal is Ui, the output signal is Uo, the open-loop gain (i.e., low-frequency gain) is Aop (s)=1+R16/R10, and the actual gain is A(s)=Uo/Ui. It should be noted that the capacitors C13 and C14 with a same value are used here. In fact, different values may be used to provide more design space.

A current equation of point A is as shown in equation (1):

$$\frac{U_i(s) - U_A(s)}{R} = \frac{U_A(s) - U_o(s)}{\frac{1}{sc}} + \frac{U_A(s) - U_B(s)}{R}. \quad (1)$$

A current equation of point B is as shown in equation (2):

$$\frac{U_A(s) - U_B(s)}{R} = \frac{U_B(s)}{\frac{1}{sc}}. \quad (2)$$

In addition, the negative input end of the amplifier U2C has the relationship shown in equation (3):

$$U_o(s) = \left(1 + \frac{R16}{R10}\right) \cdot U_B(s) = A_{op}(s) \cdot U_B(s). \quad (3)$$

Combining the above three equations, a transfer function may be obtained as shown in formula (4):

$$A(s) = \frac{U_o(s)}{U_i(s)} = \frac{A_{op}(s)}{(sRC)^2 + sRC(3 - A_{op}(s)) + 1}, \quad (4)$$

where s=jw in the above formula. Setting f0=1/(2πRC), the gain A or the open-loop gain Aop is related to s. Although Aop(s) in the circuit diagram 7A is a ratio of a resistor, a transimpedance bandpass may be designed by using a capacitor, so that a further frequency response design of the circuit may be carried out.

Since w=2πf, when f=f0, s=j/RC, and when f=f0, the gain may be as shown in formula (5):

$$A(s) = \frac{U_o(s)}{U_i(s)} = \frac{A_{op}(s)}{j(3 - A_{op}(s))}. \quad (5)$$

The magnitude of the gain is directly related to Aop(s). For example, if the open-loop gain Aop(s)=2.9, and when f=f0, the gain A=29. When the open-loop gain Aop(s)<2, the gain A may be less than the open-loop gain, at this time a convex frequency response curve cannot be obtained. In some embodiments of the present disclosure, f0=100 Hz and the open-loop gain Aop(s)=2.9 may be designed to achieve an effect that f0 is 20 dB greater than the open-loop gain (low-frequency gain). The effect of 60 dB/decade between 100 Hz and 1 KHz may be realized.

Figure 8A:
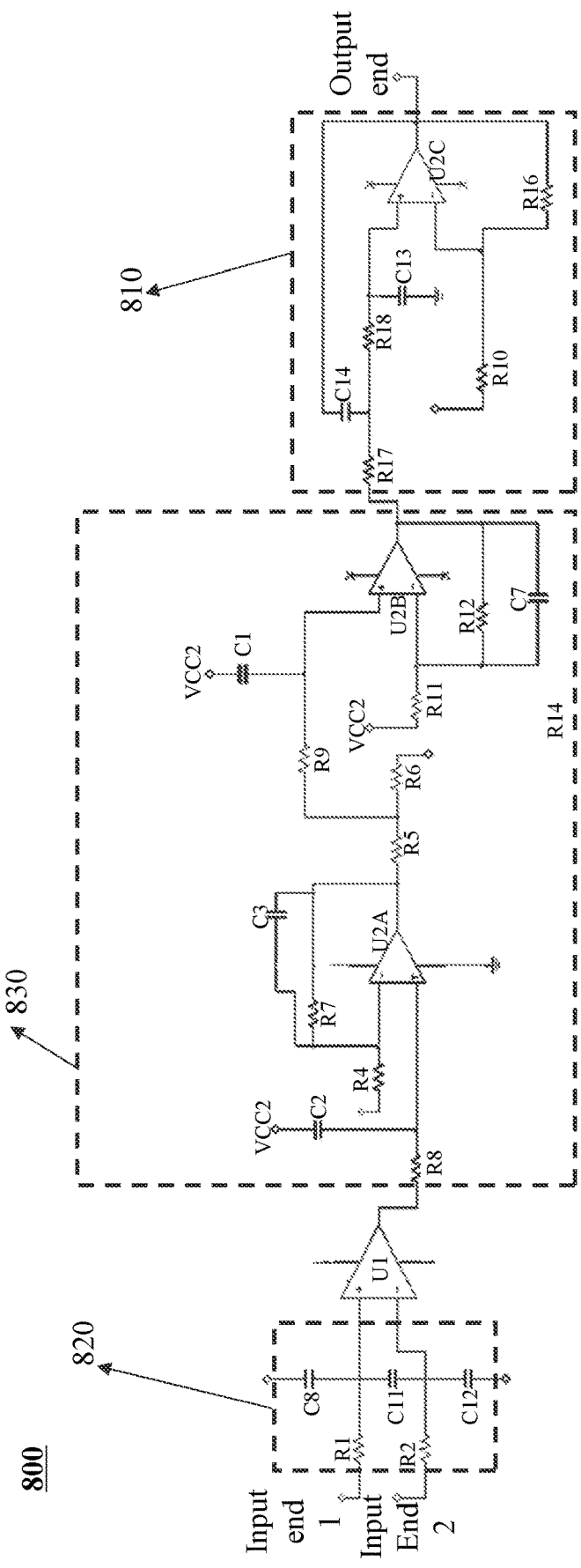
FIG. 8A is a schematic structural diagram of an exemplary low-pass filter circuit according to some embodiments of the present disclosure.
Figure 8B:
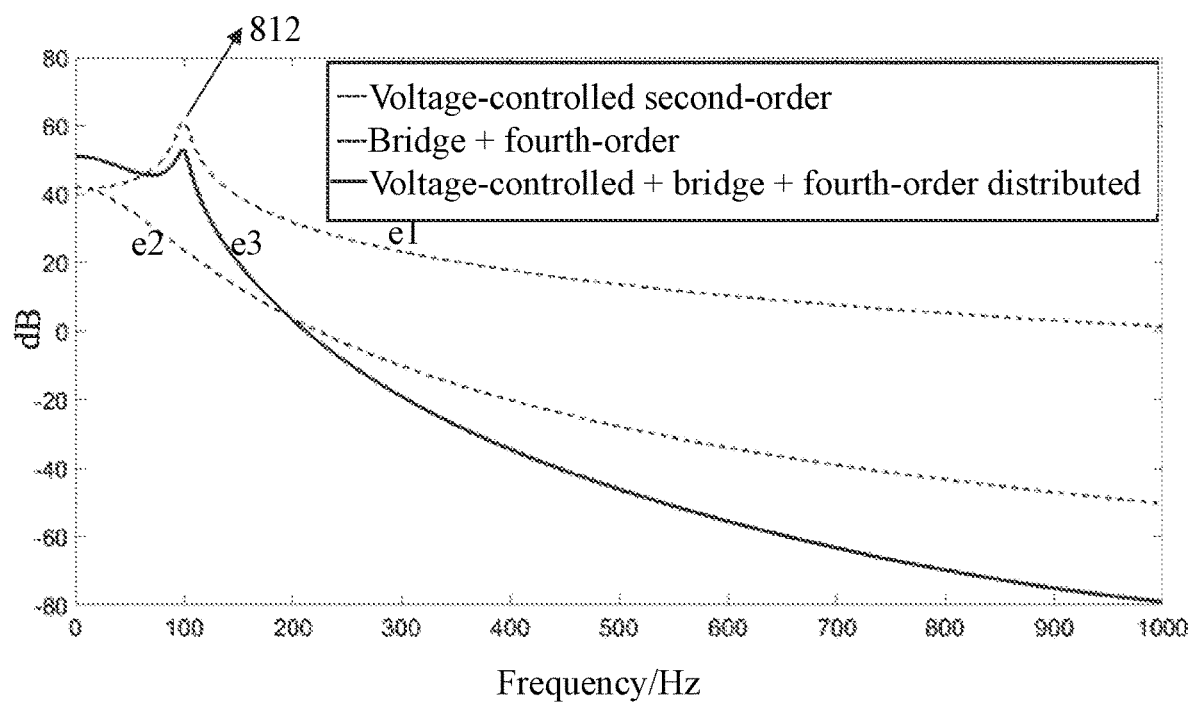
FIG. 8B is a frequency response curve diagram of the low-pass filter circuit in FIG. 8A.

FIG. 8A is a schematic structural diagram of an exemplary low-pass filter circuit according to some embodiments of the present disclosure. FIG. 8B is a frequency response curve diagram of the low-pass filter circuit in FIG. 8A.

As shown in FIG. 8A, the low-pass filter circuit 800 may include a voltage-controlled low-pass filter circuit 810, a bridge low-pass filter circuit 820, and a fourth-order low-pass filter circuit 830. In some embodiments, the low-pass filter circuit 800 may also be referred to as a threshold low-pass filter circuit. In some embodiments, the fourth-order low-pass filter circuit 830 may be implemented by two amplifiers (for example, the amplifier U2A and the amplifier U2B). Specifically, the fourth-order low-pass filter circuit 830 may be realized by a second-order distributed low-pass filter circuit and a second-order resistance capacitance low-pass filter circuit.

As shown in FIG. 8B, the curve e1 represents a frequency response curve of the voltage-controlled low-pass filter circuit 810. The curve e2 represents a frequency response curve of a circuit in which the bridge low-pass filter circuit 820 is connected in series with the fourth-order low-pass filter circuit 830. The curve e3 represents a frequency response curve of the low-pass filter circuit 800. In some embodiments, by adjusting the gain and the frequency response peak of the voltage-controlled low-pass filter circuit 810, a curve such as the curve e1 may be obtained, which may include the frequency response peak 812. By combining the circuit corresponding to the curve e1 (that is, the voltage-controlled low-pass filter circuit 810) and the circuit corresponding to the curve e2 (that is, the circuit in which the bridge low-pass filter circuit 820 is connected in series with the fourth-order low-pass filter circuit 830), a threshold low-pass filter circuit (corresponding to the curve e3) that fully retains low-frequency signals may be obtained. It may be seen from FIG. 8B that the circuit in which the bridge low-pass filter circuit 820 is connected in series with the fourth-order low-pass filter circuit 830 (corresponding to the curve e2) may have a suppression capability of 20 dB at 200 Hz relative to 100 Hz, while the threshold low-pass filter circuit 800 (corresponding to the curve e3) may have a suppression capability of about 50 dB at 200 Hz relative to 100 Hz, which may be equivalent to 31.6 times of the improvement of the suppression capability.

Figure 9A:
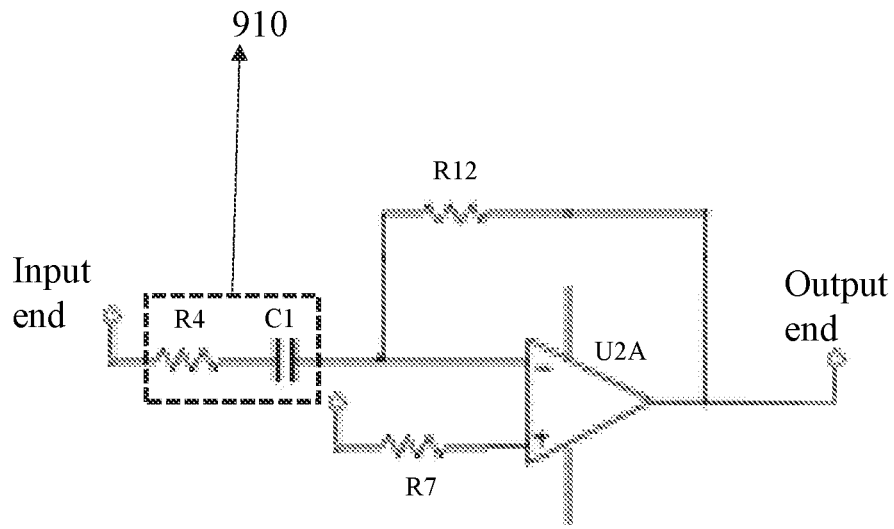
FIGS. 9A-9B are schematic structural diagrams of exemplary high-pass filter circuits according to some embodiments of the present disclosure.
Figure 9B:
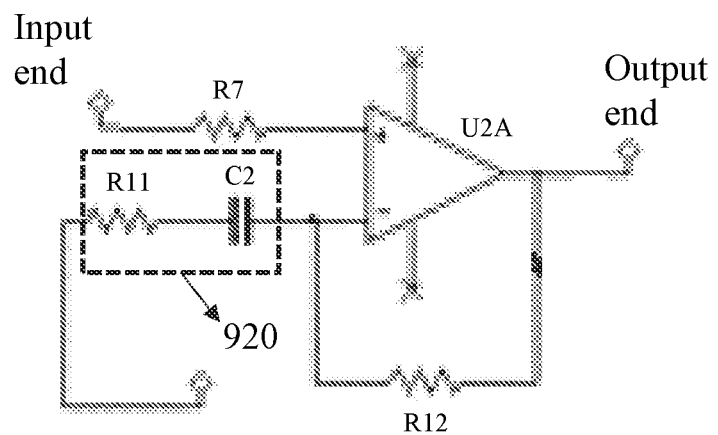
Figure 9C:
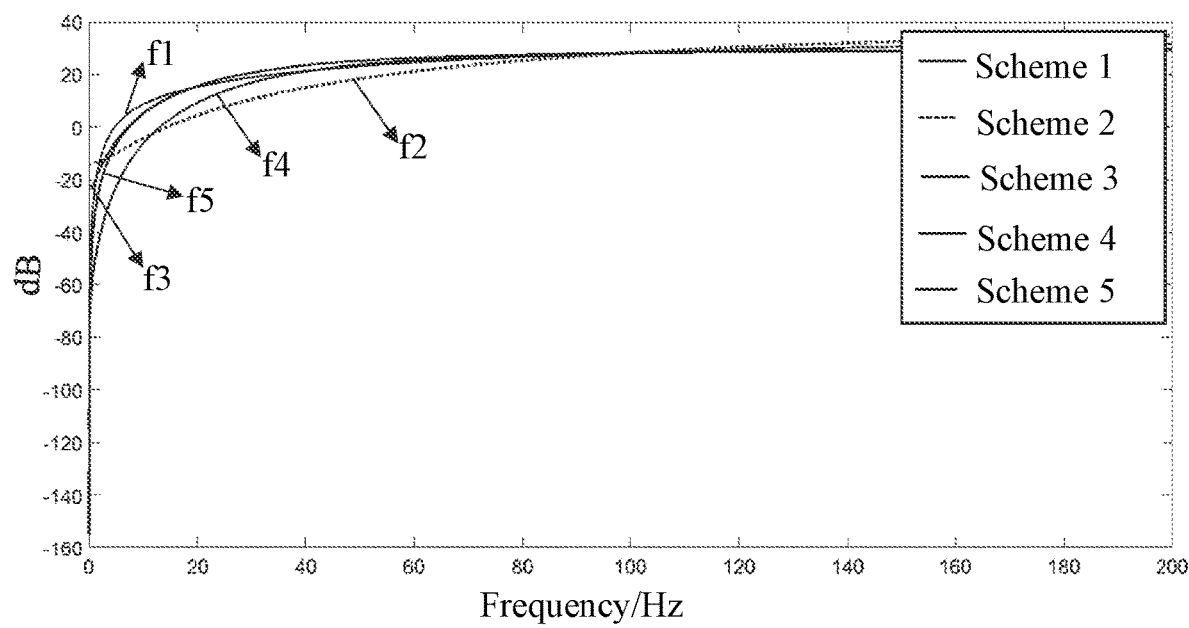
FIG. 9C is a frequency response curve diagram of the high-pass filter circuits in FIGS. 9A-9B.

FIGS. 9A-9B are schematic structural diagrams of exemplary high-pass filter circuits according to some embodiments of the present disclosure. FIG. 9C is a frequency response curve diagram of the high-pass filter circuits in FIGS. 9A-9B.

As shown in FIG. 9A, the high-pass filter circuit 900A may include a high-pass filter 910 composed of a resistor R4 and a capacitor C1, and an amplifier U2B. The first high-pass filter 910 may be connected to an input end of the amplifier U2A. In some embodiments, the first high-pass filter 910 may be located on the signal path. In some embodiments, the high-pass filter circuit 900A including one high-pass filter located on the signal path may also be referred to as a first-order main path high-pass filter circuit.

As shown in FIG. 9B, the structure of the high-pass filter circuit 900B may be similar to that of the high-pass filter circuit 900A. The difference between the high-pass filter circuit 900B and the high-pass filter circuit 900A may be that the high-pass filter 920 in the high-pass filter circuit 900B is not located on the signal path. In some embodiments, the high-pass filter circuit 900B including one high-pass filter not located on the signal path may also be called a first-order bypass high-pass filter circuit.

It should be noted that similar to the low-pass filter circuit, the high-pass filter circuit in this specification may also include a second-order or third-order high-pass filter circuit or a higher-order high-pass filter circuit, such as a second-order cascaded main path high-pass filter circuit or a second-order distributed bypass high-pass filter circuit. In some embodiments, the high-order high-pass filter circuit may include at least one first-order main path high-pass filter circuit or at least one bypass high-pass filter circuit. In some embodiments, a circuit including at least one first-order main path high-pass filter circuit and at least one bypass high-pass filter circuit may also be called a high-order hybrid high-pass filter circuit.

As shown in FIG. 9C, the curve f1 represents a frequency response curve of a first second-order distributed main path high-pass filter circuit. The curve f2 represents a frequency response curve of a first second-order distributed bypass high-pass filter circuit. The curve f3 represents a frequency response curve of a second second-order distributed bypass high-pass filter circuit, wherein parameters of the second second-order distributed bypass high-pass filter circuit may be different from parameters of the first second-order distributed bypass high-pass filter circuit. The curve f4 represents a frequency response curve of a second-order distributed hybrid high-pass filter circuit. The curve f5 represents a frequency response curve of a second second-order distributed main path high-pass filter circuit, wherein parameters of the second second-order distributed main path high-pass filter circuit may be different from parameters of the first second-order distributed main path high-pass filter circuit. It can be seen from FIG. 9C that high-pass filter circuits with different structures and/or parameters may have different frequency responses. The first second-order distributed main path high-pass filter circuit (corresponding to the curve f1) may have a strong suppression effect on signals of extremely low frequency (such as signals within 1 Hz), but its suppression effect on signals of low frequency (such as signals above 1 Hz) may be limited. The first second-order distributed bypass high-pass filter circuit (corresponding to the curve f2) and the second second-order distributed bypass high-pass filter circuit (corresponding to the curve f3) may have limited suppression effects on signals of low frequency. The second-order distributed hybrid high-pass filter circuit (corresponding to the curve f4) may have a great suppression effect on signals of extremely low frequency. For example, the second-order distributed hybrid high-pass filter circuit may suppress signals within 1 Hz better than the first second-order distributed bypass high-pass filter circuit (corresponding to the curve f2) and the second second-order distributed bypass high-pass filter circuit (corresponding to the curve f3). In addition, the second-order distributed hybrid high-pass filter circuit (corresponding to the curve f4) may also have a greater ability (stronger than the first second-order distributed main path high-pass filter circuit (corresponding to the curve f1) and the second second-order distributed main path high-pass filter circuit (corresponding to the curve f5)) to suppress signals within 5 Hz.

It should be noted that the above description of each circuit is merely for example and description, and does not limit the scope of the present disclosure. For those skilled in the art, various amendments and changes may be made to the circuit under the guidance of the present disclosure. However, these amendments and changes are still within the scope of the present disclosure. In some embodiments, since each exemplary circuit also includes an amplifier, the above exemplary circuits may amplify the signal in addition to the corresponding processing. For example, in addition to low-pass filtering the signal, the low-pass filter circuit 400A may also amplify the filtered signal. Therefore, the low-pass filter circuit 400A may also be called a low-pass filter amplifier circuit. In addition, if the amplifier in the low-pass filter amplifier circuit includes a resistance capacitance feedback network, the low-pass filter amplifier circuit may also be called a resistance capacitance low-pass filter amplifier circuit. Similarly, for example, in addition to high-pass filtering the signal, the high-pass filter circuit 900A may amplify the filtered signal. Therefore, the high-pass filter circuit 900A may also be called a high-pass filter amplifier circuit. In addition, if the amplifier in the high-pass filter amplifier circuit includes a resistance capacitance feedback network, the high-pass filter amplifier circuit may also be called a resistance capacitance high-pass filter amplifier circuit. In some embodiments, the amplification factors of all amplifiers to the signal may be the same or different. For example, the amplification factor of the amplifier to the signal may be 2 times, 4 times, 10 times, 20 times, 100 times, 300 times, 500 times, 1000 times, etc.

Figure 10A:
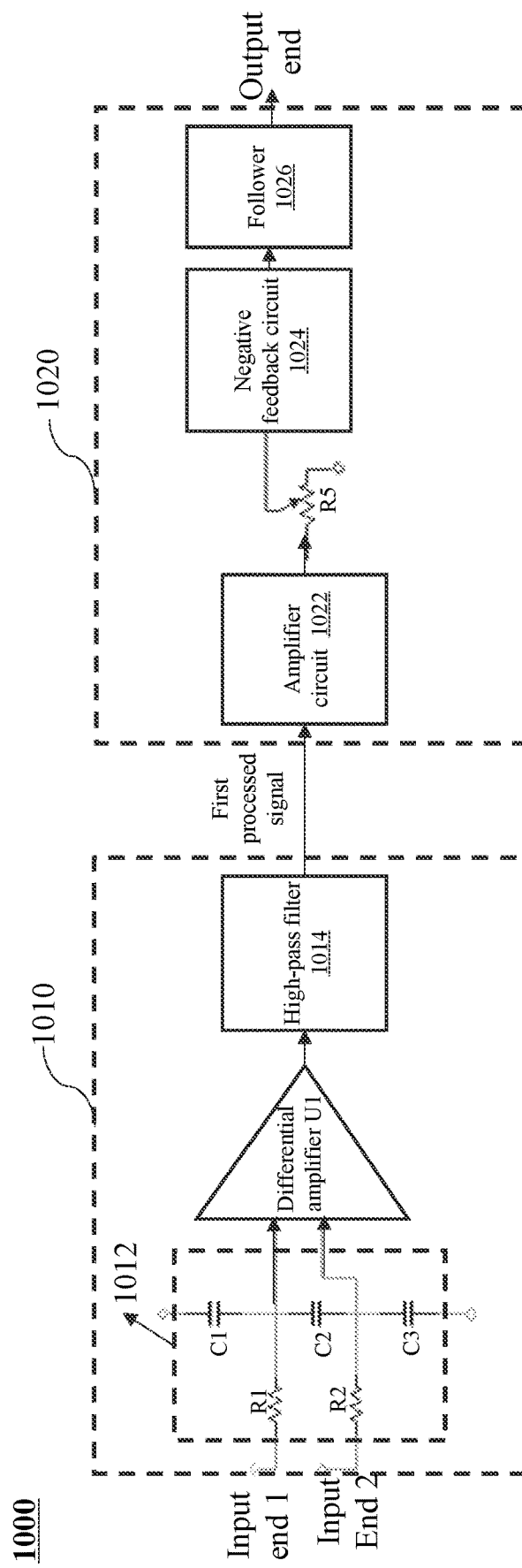
FIG. 10A is a schematic circuit diagram of an exemplary signal processing circuit according to some embodiments of the present disclosure.
Figure 10B:
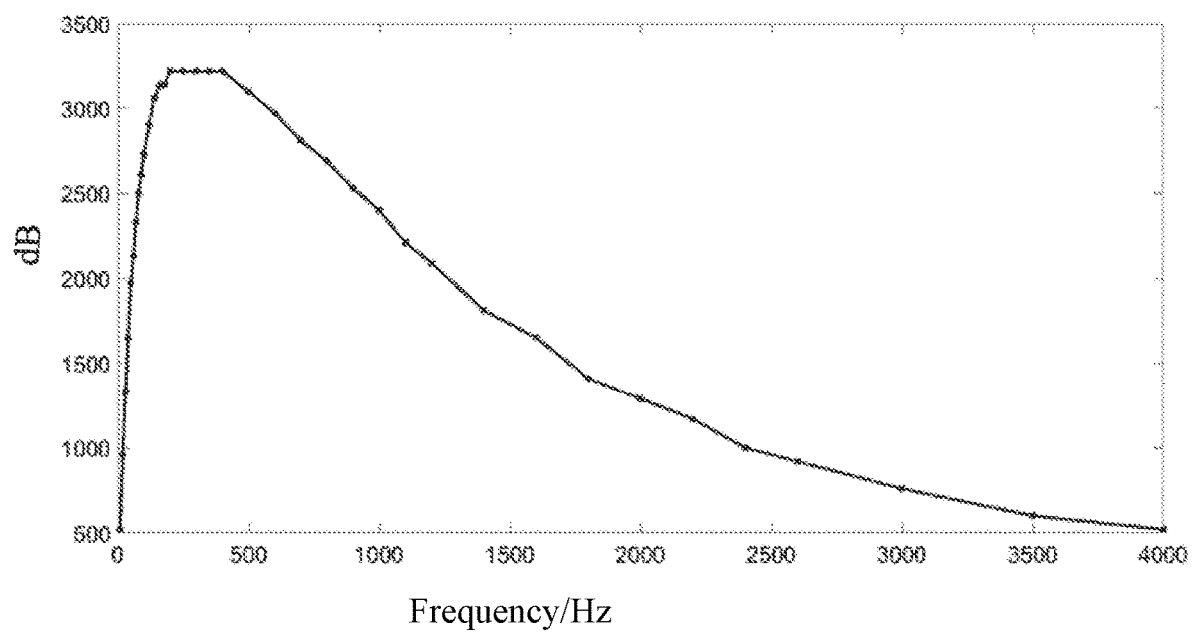
FIG. 10B is a frequency response curve of the signal processing circuit in FIG. 10A.

FIG. 10A is a schematic circuit diagram of an exemplary signal processing circuit according to some embodiments of the present disclosure. FIG. 10B is a frequency response curve of the signal processing circuit in FIG. 10A. As shown in FIG. 10A, the signal processing circuit 1000 may include a first processing circuit 1010 and a second processing circuit 1020. The second processing circuit 1020 may be directly connected to the first processing circuit 1010.

The first processing circuit 1010 may include a bridge low-pass filter circuit 1012, a differential amplifier U1, and a high-pass filter 1014. In some embodiments, the bridge low-pass filter circuit 1012 may be connected to an input end of the differential amplifier U1. The high-pass filter 1014 may be connected to an output end of the differential amplifier U1.

The first processing circuit 1010 may attenuate a noise signal in an initial signal (for example, the initial signal acquired by an electrode) and amplify a target signal in the initial signal to output a first processed signal. Specifically, the bridge low-pass filter circuit 1012 may perform low-pass filtering processing on the initial signal. For example, an upper cut-off frequency of the bridge low-pass filter circuit 1012 may be in a frequency range of 100 Hz to 1000 Hz. As another example, the upper cut-off frequency of the bridge low-pass filter circuit 1012 may be 140 Hz. A signal after being processed by the bridge low-pass filter circuit 1012 may be further processed by the differential amplifier U1. For example, the differential amplifier U1 may suppress a common mode signal (for example, the power frequency signal) in the filtered signal. As another example, the differential amplifier U1 may amplify the filtered signal. In some embodiments, the differential amplifier U1 may amplify the corresponding signal no more than 10 times. In some embodiments, the differential amplifier U1 may amplify the signal no more than 7 times. In some embodiments, the differential amplifier U1 may amplify the signal no more than 5 times. In some embodiments, the differential amplifier U1 may amplify the signal no more than 4 times. In some embodiments, the differential amplifier U1 may amplify the signal no more than 3 times. In some embodiments, the differential amplifier U1 may amplify the signal no more than twice. In the signal processing circuit as shown in FIG. 10A, since the first processing circuit 1010 only contains one amplifier (i.e., the differential amplifier U1), an amplification factor of the differential amplifier U1 may be called a first amplification factor of the first processing circuit 1010.

The high-pass filter 1014 may perform high-pass filtering processing on the signal processed by the differential amplifier U1. For example, the lower cut-off frequency of the high-pass filter 1014 may be in a frequency range of 5 Hz to 200 Hz. As another example, the lower cut-off frequency of the high-pass filter 1014 may be 20 Hz. In FIG. 10A, a signal processed by the high-pass filter 1014 may be the first processed signal.

The second processing circuit 1020 may be configured to amplify the first processed signal. In some embodiments, the second processing circuit 1020 may include an amplifier circuit 1022, a negative feedback circuit 1024, and a follower 1026. In some embodiments, the amplifier circuit 1022 may include a resistance capacitance feedback network (e.g., being composed of the resistor R7 and the capacitor C3 as shown in FIG. 6A) (that is, the amplifier circuit 1022 may also be called a resistance capacitance amplifier circuit), and a gain multiple of the second processing circuit 1020 to the first processed signal may change with the frequency of the first processed signal. The second processing circuit 1020 may amplify the first processed signal by a second amplification factor. In some embodiments, the second processing circuit 1020 may include a plurality of amplifiers, and the second amplification factor may be a total amplification factor of the plurality of amplifiers. In some embodiments, the second amplification factor may be greater than the first amplification factor. For example, the second amplification factor may be greater than 30 times, 50 times, 100 times, 200 times, 500 times, and so on. The negative feedback circuit 1024 may be configured to achieve adjustable gain (i.e., amplification factor) in a wide range using a sliding rheostat R5. For example, a gain from 0 to A may be achieved, wherein A may be a gain of the amplifier 1022. In some embodiments, the sliding rheostat R5 may also be referred to as a voltage sharing resistor. The follower 1026 may be configured to isolate an influence of the output end on the signal processing circuit 1000.

As shown in FIG. 10B, when the total gain of the signal processing circuit 1000 is high, the signal processing circuit 1000 may be easy to reach saturation when processing signals in a range of 200 Hz to 400 Hz, and the signal processing circuit 1000 may have an insufficient suppression of high-frequency signals. In some embodiments, the frequency response (i.e., the bandpass effect) of the signal processing circuit 1000 may be optimized by adjusting the resistance and capacitance values in the resistance capacitance feedback network in the amplifier circuit 1022. For example, the resistance value in the resistance capacitance feedback network may be increased by 2 times and the capacitance value may be reduced by 2 times. In some embodiments, in order to optimize the frequency response of the high-pass filter 1014 in the signal processing circuit 1000, values of the resistor and the capacitor in the high-pass filter 1014 may be adjusted non-proportionally to expand the influence of the capacitor (for example, only increase the value of the capacitor). However, at this time, signals not in the target frequency band may also be gained.

In some embodiments, since increasing an order of a circuit may increase a frequency response steepness of the circuit (that is, only a signal within the target frequency band may be greatly improved and a signal not within the target frequency band may be suppressed), in order to improve the frequency response steepness of the signal processing circuit 1000, a higher order signal processing circuit may be designed on the basis of the signal processing circuit 1000. For more descriptions, please refer to FIG. 11 and the descriptions thereof, which will not be repeated here.

Figure 11:
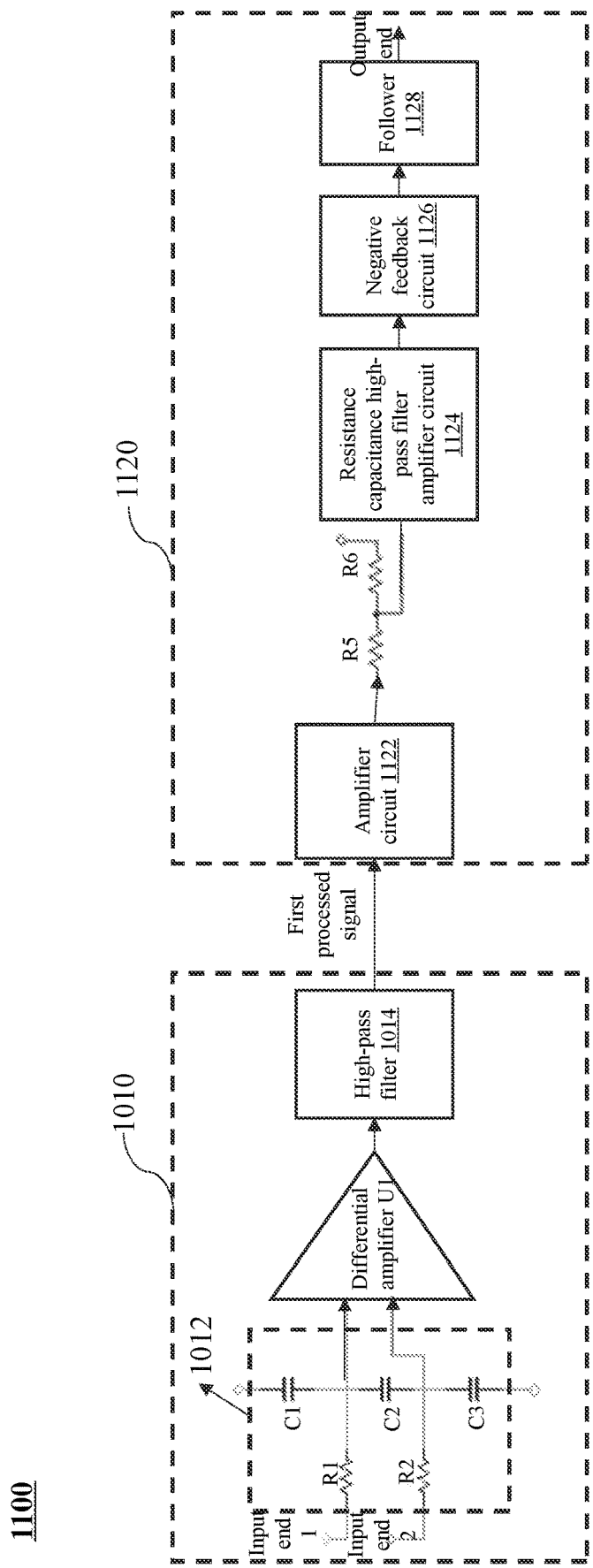
FIG. 11 is a schematic circuit diagram of an exemplary signal processing circuit according to some embodiments of the present disclosure.

FIG. 11 is a schematic circuit diagram of an exemplary signal processing circuit according to some embodiments of the present disclosure. As shown in FIG. 11, the signal processing circuit 1100 may include the same first processing circuit 1010 as the signal processing circuit 1000. The signal processing circuit 1100 may also include a second processing circuit 1120.

The second processing circuit 1120 may include an amplifier circuit 1122, a resistance capacitance high-pass filter amplifier circuit 1124, a negative feedback circuit 1126, and a follower 1128. For the circuit architecture, compared with the second processing circuit 1020 in the signal processing circuit 1000, the second processing circuit 1120 in the signal processing circuit 1100 may further include a resistance capacitance high-pass filter amplifier circuit 1124, which may include a high-pass filter, thereby playing a role of high-pass filtering on the signal. The resistance capacitance high-pass filter amplifier circuit 1124 may also include a resistance capacitance feedback network, which is composed of a capacitor and a resistor connected in parallel and arranged between an input end and the output end of the amplifier. In some embodiments, the signal processing circuit 1100 may also be referred to as a second-order filtered EMG processing circuit. Further, compared with the second processing circuit 1020, in the second processing circuit 1120, the sliding rheostat R5 in the second processing circuit 1020 may be replaced by the resistor R5 and the resistor R6.

In some embodiments, in order to optimize the frequency response (for example, the suppression of 1 Hz and 50 Hz may be stronger, and the frequency response peak may be kept within 500 Hz, and the gain may be 400-600 times), parameters of the amplifier circuit 1222 may be adjusted to change a gain of the second processing circuit 1120 on the signal. For example, the resistor R7 and the capacitor C8 may be reduced in a same proportion.

FIG. 12A is a schematic circuit diagram of an exemplary signal processing circuit according to some embodiments of the present disclosure. FIG. 12B illustrates a frequency response curve when a frequency response peak of the signal processing circuit in FIG. 12A is 80 Hz.

As shown in FIG. 12A, the signal processing circuit 1200 may include a first processing circuit 1210 and a second processing circuit 1220. The second processing circuit 1220 may be directly connected to the first processing circuit 1210.

In some embodiments, the first processing circuit 1210 may include a bridge low-pass filter circuit 1212, a differential amplifier U1, and a notch circuit 1214. The bridge low-pass filter circuit 1212 and the differential amplifier U1 may have same structures as the bridge low-pass filter circuit 1012 and the differential amplifier U1 in the signal processing circuit 1000. The notch circuit 1214 may include a dual-T active notch circuit. In some embodiments, a notch point frequency of the notch circuit 1214 may be set to the frequency (for example, 50 Hz) of the power frequency signal. In some embodiments, the notch circuit 1214 may also include a cascaded notch circuit. Further, the notch circuit 1214 may include a multi-cascaded notch circuit. The notch point frequencies of the multiple notch circuits in the mufti-cascaded notch circuit may be set to 50 Hz, 100 Hz, 150 Hz, 250 Hz, etc.

The second processing circuit 1220 may include a resistance capacitance high-pass filter amplifier circuit 1222, a resistance capacitance low-pass filter amplifier circuit 1224, a voltage-controlled low-pass filter circuit 1226, a negative feedback circuit 1128, and a follower 1229. The resistance capacitance high-pass filter amplifier circuit 1222, the resistance capacitance low-pass filter amplifier circuit 1224, the voltage-controlled low-pass filter circuit 1226, and the follower 1229 may be connected in series successively. The resistance capacitance high-pass filter amplifier circuit 1222 may perform high-pass filtering and amplification processing on a signal. The resistance capacitance low-pass filter amplifier circuit 1224 may perform low-pass filtering and amplification processing on a signal. The amplifier in the resistance capacitance high-pass filter amplifier circuit 1222 and the amplifier in the resistance capacitance low-pass filter amplifier circuit 1224 may have the same or different signal amplification capabilities. In some embodiments, the amplifier may amplify the signal by more than 10 times. In some embodiments, the amplifier may amplify the signal by more than 30 times. In some embodiments, the amplifier may amplify the signal by more than 100 times. In some embodiments, the amplifier may amplify the signal by more than 500 times. The voltage-controlled low-pass filter circuit 1226 may be combined with the bridge low-pass filter circuit 1212 and/or the resistance capacitance low-pass filter amplifier circuit 1224 to compensate for the attenuation of the bridge low-pass filter circuit 1212 and/or the resistance capacitance low-pass filter amplifier circuit 1224 near its upper cut-off frequency, so as to make the passband flatter.

In the second processing circuit 1220, the resistor R5 and the resistor R6 may also be referred to as voltage sharing resistors. The frequency response of the signal processing circuit 1200A may be adjusted by adjusting the resistance values of the voltage sharing resistors. For example, a resistance value of the voltage sharing resistor may be increased to prevent the target signal loss caused by signal saturation (especially noise signal saturation).

As shown in FIG. 12B, the curve g0 represents a frequency response curve of a traditional signal processing product. The curve g1 represents a frequency response curve of the signal processing circuit 1200 when the voltage sharing resistor has a first resistance value, and the curve g2 represents a frequency response curve of the signal processing circuit 1200 when the voltage sharing resistor has a second resistance value. The second resistance value may be greater than the first resistance value. It can be seen from FIG. 12B that due to the existence of the notch circuit 1214 for the power frequency signal (50 Hz), the curve g1 and the curve g2 may have depressions at 50 Hz, that is, the power frequency signal may be greatly suppressed. When the frequency response peak of the signal processing circuit 1200 is set to 80 Hz, compared with a traditional signal processing product, the signal processing circuit 1200 may contain less noise signals, and signals in the high-frequency range may be effectively suppressed.

In some embodiments, based on a principle of giving priority to the processing of the power frequency signal, the power frequency harmonic signals, the MA, etc., and then making a relatively large gain, the signal processing circuit 1200A may be adjusted as shown in FIG. 12C.

Figure 12D:
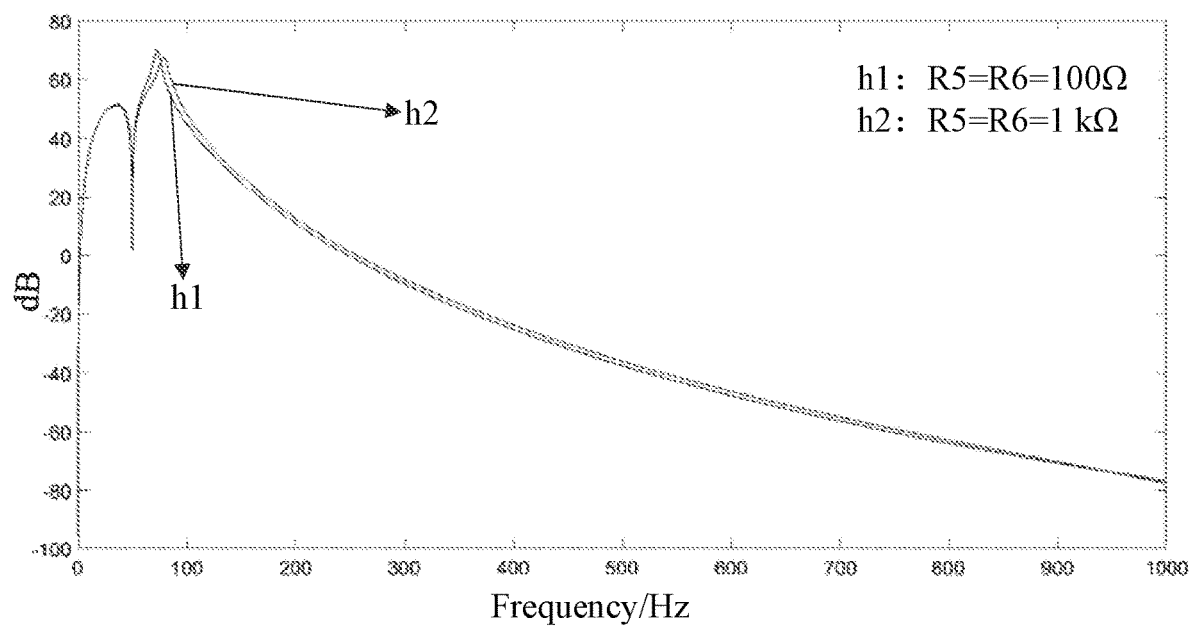
FIG. 12D illustrates a frequency response curve when the frequency response peak of the signal processing circuit in FIG. 12C is 80 Hz.

FIG. 12C is a schematic circuit diagram of an exemplary signal processing circuit according to some embodiments of the present disclosure. FIG. 12D illustrates a frequency response curve when the frequency response peak of the signal processing circuit in FIG. 12C is 80 Hz. As shown in FIG. 12C, the voltage-controlled low-pass filter circuit 1226 in the second processing circuit 1220 may be connected before the resistance capacitance high-pass filter amplifier circuit 1222, while the resistance capacitance low-pass filter amplifier circuit 1224 may be directly connected with the negative feedback circuit 1228. In some embodiments, when the voltage-controlled low-pass filter circuit 1226 is set immediately after the notch circuit 1214, the voltage-controlled low-pass filter circuit 1226 may also be considered to be set in the first processing circuit.

As shown in FIG. 12D, the curve h1 represents a frequency response curve of the signal processing circuit 1200C when the voltage sharing resistors R5=R6=1000. The curve h2 represents a frequency response curve of the signal processing circuit 1200C when the voltage sharing resistors R5=R6=1Ω. It may be seen from FIG. 12D that when resistance values of the voltage sharing resistor R5 and the voltage sharing resistor R6 increase (for example, from 1000 to 1 kΩ), the strength of the frequency response peak of the signal processing circuit 1200C may be reduced. In addition, the frequency response peak of the signal processing circuit 1200C may be moved to high frequency.

Figure 13:
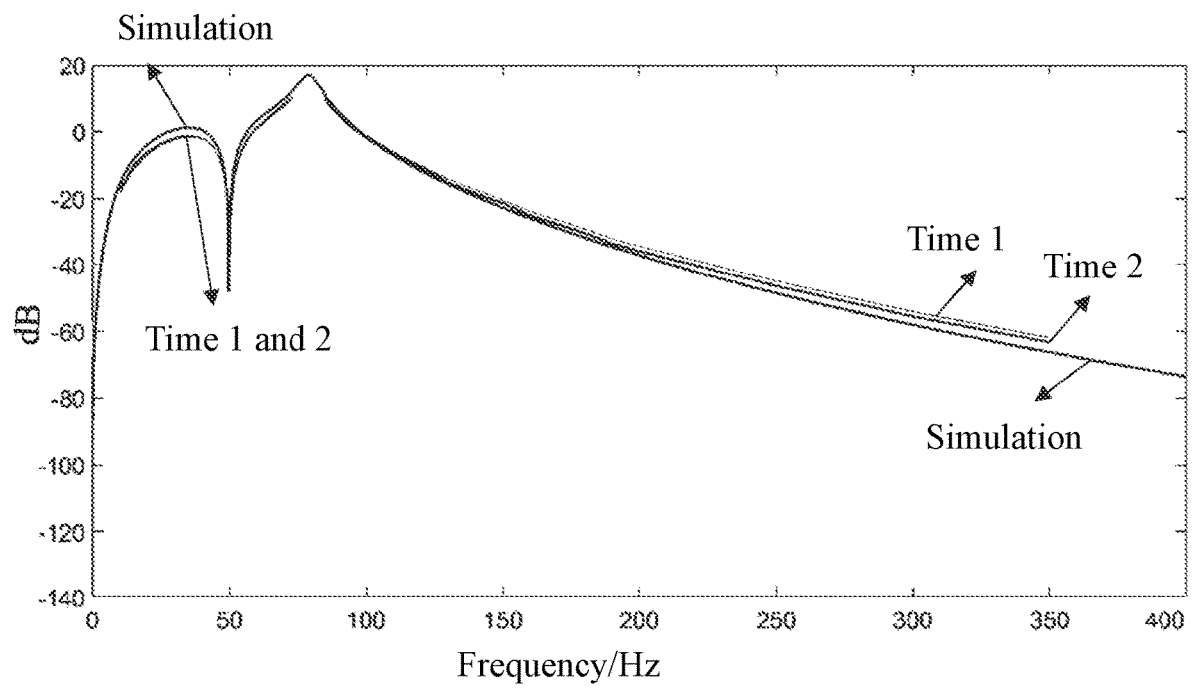
FIG. 13 is a comparison diagram between frequency response curves of a signal processing circuit measured at different times and a simulated frequency response curve of the signal processing circuit according to some embodiments of the present disclosure.

FIG. 13 is a comparison diagram between frequency response curves of a signal processing circuit measured at different times and a simulated frequency response curve of the signal processing circuit according to some embodiments of the present disclosure. In some embodiments, in order to test a stability of the signal processing circuit in the embodiments of the present disclosure, one electrode in the acquisition circuit may be raised in half (that is, the electrode is half off) or all (that is, the electrode is completely off) when acquiring the EMG signal.

As shown in FIG. 13, the time 1 curve and the time 2 curve are measured at different times and under different electrode shedding conditions. In a process of obtaining the time 1 curve, the signal acquisition electrode may be raised in half, while in a process of obtaining the time 2 curve, the electrode may not be raised. It may be seen from FIG. 13 that using the same signal processing circuit, the frequency response curved of the signal processing circuit measured at different times (for example, the time 1 and the time 2) and under different conditions (electrode half falling off or not falling off) may be highly consistent, have little difference with the simulation signal, and there is no signal saturation problem. Therefore, the signal processing circuit in the embodiments of the present disclosure may have strong stability and high accuracy, and may deal with a problem of electrode falling off to a large extent during a test.

Figure 14:
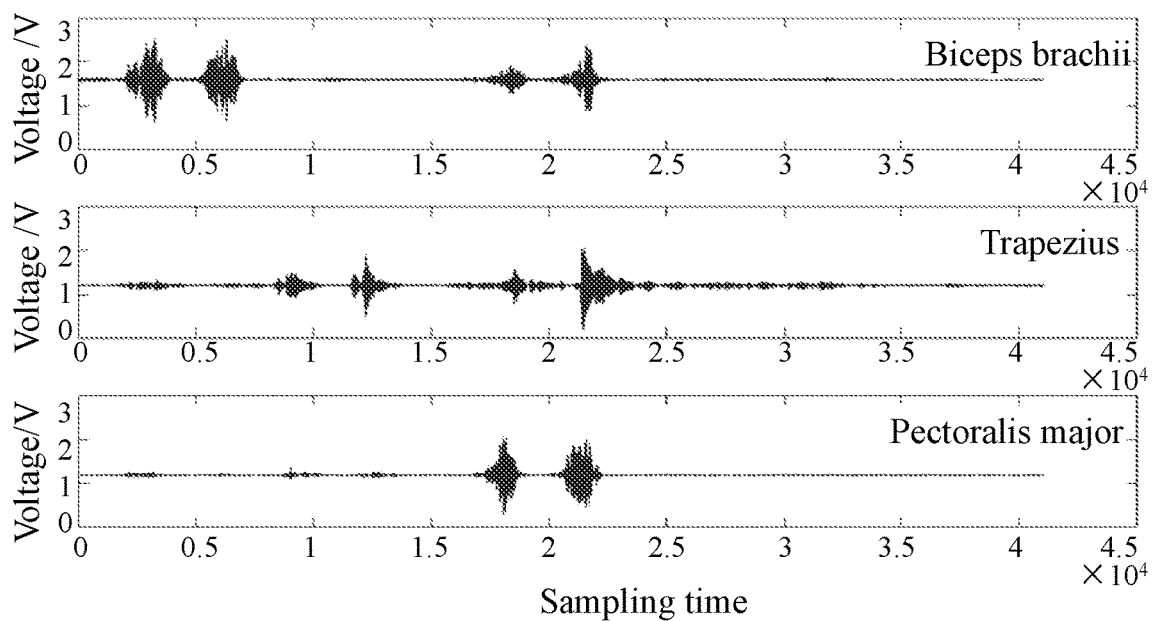
FIG. 14 illustrates electromyographic signals acquired during a bicep curl experiment using a signal processing circuit according to some embodiments of the present disclosure.

FIG. 14 illustrates electromyographic signals acquired during a bicep curl experiment using a signal processing circuit according to some embodiments of the present disclosure. From top to bottom, FIG. 14 shows signal data acquired from biceps brachii, trapezius, and pectoralis major, respectively. In a process of the bicep curl experiment, the subjects' actions may be two normal bicep curl actions, two shoulder shrugging actions, and two chest pinching actions in turn. It can be seen from FIG. 14 that a signal processed by the signal processing circuit may have a high signal-to-noise ratio (the signal-to-noise ratio may reach a 500-level), the power frequency and its harmonics may be greatly suppressed, and the EMG signal components may become simple (mainly including signals of the target frequency band). Therefore, the signal processing circuit in the embodiments of the present disclosure may successfully complete a high-quality acquisition of the EMG signal in the bicep curl experiment.

The possible beneficial effects of the embodiments of the present disclosure may include but be not limited to: (1) by using time-sharing multiplexing, the purpose of saving space cost and reducing hardware requirements may be achieved under a condition of ensuring the acquisition and processing of multiple signal sources; (2) when multiple input channels have signals at a same time, crosstalk between the input channels may be reduced; (3) the complete reconstruction strategy may completely reproduce the corresponding multiple target signals based on the sampled data; (4) under the strength characterization strategy, strength information, and partial frequency information of the target signal may be obtained based on the acquired sampled data; (5) the problem of possible baseline drift may be solved by an ADC with small gain and high-precision, a programmed baseline, and adding a high-pass filter circuit; (6) by first processing noise signals with high strength such as the power frequency signal and the power frequency harmonic signals, and then making a greater gain, the target signals may be prevented from being lost due to signal oversaturation; (7) by setting a frequency response peak of the circuit far away from the frequency of the power frequency signal, the power frequency signal may be further suppressed; (8) by adding a capacitor in parallel with a resistor in the feedback network of the feedback amplifier circuit, a signal gain of the feedback amplifier circuit may change with the frequency.

It should be noted that different embodiments may have different beneficial effects. In different embodiments, the beneficial effects may be any one or a combination of the above, or any other beneficial effects that may be obtained.

The basic concepts have been described above. Obviously, for those skilled in the art, the above detailed disclosure may be only an example and does not constitute a limitation of the present disclosure. Although it may be not explicitly stated here, those skilled in the art may make various modifications, improvements, and amendments to the present disclosure. Such modifications, improvements and amendments are suggested in the present disclosure, so such modifications, improvements and amendments still belong to the spirit and scope of the exemplary embodiments of the present disclosure.

Meanwhile, the present disclosure uses specific words to describe the embodiments of the present disclosure. For example, "one embodiment," and/or "some embodiments" mean a certain feature or structure related to at least one embodiment of the present disclosure. Therefore, it should be emphasized and noted that "one embodiment" or "an alternative embodiment" mentioned twice or more in different positions in the present disclosure does not necessarily refer to the same embodiment. In addition, certain features or structures in one or more embodiments of the present disclosure may be appropriately combined.

In addition, those skilled in the art can understand that various aspects of the present disclosure can be described and described through a number of patentable categories or situations, including any new and useful combination of processes, machines, products or substances, or any new and useful improvements to them. Accordingly, various aspects of the present disclosure can be completely executed by hardware, software (including firmware, resident software, microcode, etc.), or a combination of hardware and software. The above hardware or software can be referred to as "data block," "module," "engine," "unit," "component" or "system". Further, various aspects of the present disclosure may be embodied in a computer product located in one or more computer-readable media, which includes computer-readable program coding.

In addition, unless explicitly stated in the claims, the sequence of processing elements and sequences, the use of numbers and letters, or the use of other names described in the present disclosure are not configured to define the sequence of processes and methods in the present disclosure. Although the above disclosure has discussed some currently considered useful embodiments of the invention through various examples, it should be understood that such details are only for the purpose of explanation, and the additional claims are not limited to the disclosed embodiments. On the contrary, the claims are intended to cover all amendments and equivalent combinations that conform to the essence and scope of the embodiments of the present disclosure. For example, although the system components described above may be implemented by hardware devices, they may also be implemented only by software solutions, such as installing the described system on an existing server or mobile device.

Similarly, it should be noted that, in order to simplify the description disclosed in the present disclosure and thus help the understanding of one or more embodiments of the invention, the foregoing description of the embodiments of the present disclosure sometimes incorporates a variety of features into one embodiment, the drawings or the description thereof. However, this disclosure method does not mean that the object of the present disclosure requires more features than those mentioned in the claims. In fact, the features of the embodiments are less than all the features of the single embodiments disclosed above.

In some embodiments, numbers describing the number of components and attributes are used. It should be understood that such numbers used in the description of embodiments are modified by the modifier "about," "approximate" or "generally" in some examples. Unless otherwise stated, "approximately" or "generally" indicate that a ±20% change in the figure may be allowed. Accordingly, in some embodiments, the numerical parameters used in the description and claims are approximate values, and the approximate values may be changed according to the characteristics required by individual embodiments. In some embodiments, the numerical parameter should consider the specified significant digits and adopt the method of general digit reservation. Although the numerical fields and parameters configured to confirm the range breadth in some embodiments of the present disclosure are approximate values, in specific embodiments, the setting of such values may be as accurate as possible within the feasible range.

For each patent, patent application, patent application disclosure and other materials cited in the present disclosure, such as articles, books, specifications, publications, documents, etc., the entire contents are hereby incorporated into the present disclosure for reference. Except for the present disclosure history documents that are inconsistent with or conflict with the contents of the present disclosure, and the documents that limit the widest range of claims in the present disclosure (currently or later appended to the present disclosure). It should be noted that in case of any inconsistency or conflict between the description, definitions, and/or use of terms in the supplementary materials of the present disclosure and the contents described in the present disclosure, the description, definitions, and/or use of terms in the present disclosure shall prevail.

Finally, it should be understood that the embodiments described in the present disclosure are only configured to illustrate the principles of the embodiments of the present disclosure. Other deformations may also fall within the scope of the present disclosure. Therefore, as an example rather than a limitation, the alternative configuration of the embodiments of the present disclosure may be regarded as being consistent with the teachings of the present disclosure. Accordingly, the embodiments of the present disclosure are not limited to those explicitly introduced and described in the present disclosure.

What is claimed is:

1. A signal processing circuit, comprising an analog circuit configured to process an initial signal received by the analog circuit, the initial signal comprising a target signal and a noise signal, wherein the analog circuit comprises:
   a first processing circuit, configured to increase a ratio of the target signal to the noise signal and output a first processed signal; and
   a second processing circuit connected to the first processing circuit, configured to amplify the first processed signal, wherein a gain multiple of the second processing circuit to the first processed signal varies with a frequency of the first processed signal, wherein:
      the first processing circuit includes a common mode signal suppression circuit, a low-pass filter circuit, and a high-pass filter circuit,
      the common mode signal suppression circuit is configured to suppress a common mode signal in the initial signal.

2. The signal processing circuit of claim 1, wherein the common mode signal suppression circuit comprises a differential amplifier.

3. The signal processing circuit of claim 2, wherein the low-pass filter circuit includes a bridge circuit structure formed at an input end of the differential amplifier.

4. The signal processing circuit of claim 2, wherein an input impedance of the differential amplifier is greater than 10 MΩ.

5. The signal processing circuit of claim 1, wherein an upper cut-off frequency point of the low-pass filter circuit is within a frequency range of 100 Hz-1000 Hz.

6. The signal processing circuit of claim 1, wherein a lower cut-off frequency point of the high-pass filter circuit is within a frequency range of 5 Hz-200 Hz.

7. The signal processing circuit of claim 1, wherein the first processing circuit comprises a notch circuit for suppressing a power frequency signal.

8. The signal processing circuit of claim 7, wherein the notch circuit comprises a cascaded notch circuit, and the cascaded notch circuit is also configured to suppress one or more harmonics in the power frequency signal.

9. The signal processing circuit of claim 7, wherein the notch circuit comprises a dual-T active notch circuit.

10. The signal processing circuit of claim 1, wherein the first processing circuit further comprises a voltage-controlled low-pass filter circuit, and the voltage-controlled low-pass filter circuit is configured to provide a gain near a target frequency of the voltage-controlled low-pass filter circuit and is combined with the low-pass filter circuit to compensate an attenuation of the low-pass filter circuit.

11. The signal processing circuit of claim 1, wherein the increasing the ratio of the target signal to the noise signal by the first processing circuit comprises:
   performing amplification processing of a first amplification factor on the target signal; and
   performing attenuation processing on the noise signal.

12. The signal processing circuit of claim 11, wherein the second processing circuit comprises an amplifier circuit, a feedback circuit, and a follower,
   the amplifier circuit is configured to amplify the first processed signal by a second amplification factor, the second amplification factor being greater than the first amplification factor, and
   the follower is configured to isolate an influence of an output end of the signal processing circuit.

13. The signal processing circuit of claim 1, wherein the second processing circuit has a greater gain response to the first processed signal in a first frequency range than that of a frequency range outside the first frequency range.

14. The signal processing circuit of claim 13, wherein the first frequency range includes 20 Hz-140 Hz.

15. The signal processing circuit of claim 1, wherein the initial signal comprises a myoelectric signal.

16. The signal processing circuit of claim 1, further comprising: a control circuit, a switch circuit, and at least two signal acquisition circuits, wherein,
   the at least two signal acquisition circuits are configured to acquire at least two initial signals;
   the switch circuit is configured to control a conduction between the at least two signal acquisition circuits and the analog circuit, so that initial signals acquired by a part of the at least two signal acquisition circuits are transmitted to the analog circuit at the same time; and
   the control circuit is configured to receive the target signal processed by the analog circuit, and sample the processed target signal.

17. The signal processing circuit of claim 16, wherein the switch circuit includes a plurality of input channels, each signal acquisition circuit in the at least two signal acquisition circuits is independently connected to one input channel, and the switch circuit selects only one input channel to be conducted at the same time based on a control signal of the control circuit.

18. A signal processing device, comprising: a signal processing circuit the signal processing circuit comprising an analog circuit configured to process an initial signal received by the analog circuit, the initial signal comprising a target signal and a noise signal, wherein the analog circuit comprises:
- a first processing circuit, configured to increase a ratio of the target signal to the noise signal and output a first Processed signal; and
- a second processing circuit connected to the first processing circuit, configured to amplify the first processed signal, wherein a gain multiple of the second processing circuit to the first processed signal varies with a frequency of the first processed signal, wherein:
    - the first processing circuit includes a common mode signal suppression circuit, a low-pass filter circuit, and a high-pass filter circuit,
    - the common mode signal suppression circuit is configured to suppress a common mode signal in the initial signal.

19. The signal processing device of claim 18, wherein the common mode signal suppression circuit comprises a differential amplifier.

20. The signal processing device of claim 19, wherein the low-pass filter circuit includes a bridge circuit structure formed at an input end of the differential amplifier.

* * * * *